United States Patent
Holden et al.

(10) Patent No.: US 12,318,324 B2
(45) Date of Patent: Jun. 3, 2025

(54) OSTOMY APPLIANCE

(71) Applicant: ConvaTec Limited, Flintshire (GB)

(72) Inventors: Clare Holden, Flintshire (GB); Alice Young, Flintshire (GB); Kevin Evans, Flintshire (GB)

(73) Assignee: CONVATEC LIMITED, Flintshire (GB)

(*) Notice: Subject to any disclaimer, the term of this patent is extended or adjusted under 35 U.S.C. 154(b) by 704 days.

(21) Appl. No.: 17/335,644

(22) Filed: Jun. 1, 2021

(65) Prior Publication Data

US 2021/0369486 A1  Dec. 2, 2021

Related U.S. Application Data

(63) Continuation of application No. PCT/GB2021/051336, filed on Jun. 1, 2021.

(30) Foreign Application Priority Data

Jun. 2, 2020 (GB) .................................. 2008232

(51) Int. Cl.
*A61F 5/441* (2006.01)
*A61F 5/44* (2006.01)
(Continued)

(52) U.S. Cl.
CPC ............ *A61F 5/441* (2013.01); *A61F 5/4404* (2013.01); *A61F 5/442* (2013.01); *A61F 5/443* (2013.01)

(58) Field of Classification Search
CPC ........ A61F 5/445; A61F 5/441; A61F 5/4404; A61F 5/442; A61F 5/443
See application file for complete search history.

(56) References Cited

U.S. PATENT DOCUMENTS 11,033,420 B2   6/2021  Blatt
11,191,662 B2   12/2021 Cesa et al.
(Continued)

FOREIGN PATENT DOCUMENTS

DE    102014104737 A1   10/2015
EP      1557145 A2       7/2005
(Continued)

OTHER PUBLICATIONS

International Search Report; European Patent Office; International Application No. PCT/GB2021/051336; Sep. 16, 2021; 4 pages.
(Continued)

*Primary Examiner* — Jessica Arble
*Assistant Examiner* — Hans Kaliher
(74) *Attorney, Agent, or Firm* — TAFT STETTINIUS HOLLISTER LLP; Ryan O. White; Derek B. Lavender

(57) ABSTRACT

An ostomy appliance comprising an inner wall and an outer wall that define a cavity for containing a stomal output, the ostomy appliance having an upper section, a lower section and a waisted section that is located between the upper section and the lower section. The upper section has a maximum width (A) that is greater than a maximum width (B) of the lower section and the waisted section has a minimum width (C) that is less than the maximum width (B) of the lower section. The waisted section has a left-hand edge that is smoothly rounded and a right-hand edge that is smoothly rounded, and both the left-hand edge and the right-hand edge smoothly blend, respectively, into left-hand edges and right-hand edges of the upper section and the lower section.

19 Claims, 21 Drawing Sheets

(51) Int. Cl.
*A61F 5/442* (2006.01)
*A61F 5/443* (2006.01)

(56) References Cited

U.S. PATENT DOCUMENTS

| | | | |
|---|---|---|---|
| 11,229,543 B2 | 1/2022 | Cesa et al. | |
| 11,234,856 B2 | 2/2022 | Cisko, Jr. et al. | |
| 11,246,739 B2 | 2/2022 | Ekfeldt et al. | |
| 11,389,319 B2 | 7/2022 | Botten et al. | |
| 11,491,043 B2 | 11/2022 | Langhorn et al. | |
| 11,819,445 B2 | 11/2023 | Langhorn et al. | |
| 2005/0177119 A1* | 8/2005 | Tsai | A61F 5/448 604/332 |
| 2011/0028924 A1 | 2/2011 | Murray | |
| 2011/0190718 A1* | 8/2011 | Wheaton | A61F 5/445 604/332 |
| 2013/0253455 A1* | 9/2013 | Masters | A61F 5/445 604/332 |
| 2014/0163497 A1* | 6/2014 | Hannan | A61F 5/443 156/60 |
| 2020/0390590 A1* | 12/2020 | O'Grady | A61F 5/4405 |
| 2021/0177642 A1 | 6/2021 | Andersen et al. | |
| 2021/0244497 A1 | 8/2021 | Taweh | |
| 2021/0369484 A1 | 12/2021 | Holden et al. | |
| 2021/0369485 A1 | 12/2021 | Evans | |
| 2021/0369486 A1 | 12/2021 | Holden et al. | |
| 2021/0369491 A1 | 12/2021 | Holden | |
| 2021/0369493 A1 | 12/2021 | Young et al. | |
| 2021/0369494 A1 | 12/2021 | Holden et al. | |
| 2022/0096262 A1 | 3/2022 | Austin | |
| 2022/0168132 A1 | 6/2022 | Jewell | |
| 2022/0226143 A1 | 7/2022 | Negrete | |
| 2022/0110778 A1 | 10/2022 | Liu et al. | |
| 2022/0339022 A1 | 10/2022 | Weche | |
| 2023/0081026 A1* | 3/2023 | Mahood | A61F 5/443 604/344 |
| 2023/0218424 A1 | 7/2023 | Armstrong | |
| 2023/0255814 A1 | 8/2023 | Donovan et al. | |
| 2023/0355425 A1 | 11/2023 | Scott | |

FOREIGN PATENT DOCUMENTS

| | | |
|---|---|---|
| EP | 3837520 A1 | 6/2021 |
| EP | 3454796 B1 | 2/2022 |
| EP | 3454797 B1 | 2/2022 |
| EP | 3955864 A1 | 2/2022 |
| EP | 3998052 A1 | 5/2022 |
| EP | 2942039 B1 | 7/2022 |
| EP | 3955864 B1 | 1/2024 |
| EP | 3541332 B1 | 3/2024 |
| FR | 2507888 A1 | 12/1982 |

OTHER PUBLICATIONS

Written Opinion of the International Searching Authority; European Patent Office; International Application No. PCT/GB2021/051336; Sep. 16, 2021; 7 pages.

* cited by examiner

Example 1

Example 2

Example 3

Example 4

Example 5

Example 6

Example 7

Example 8

Example 9

| Example | Appliance Volume | | Measurements when appliance was filled to 75% capacity (mm) | | | | | Y1/75% (mm/ml) | Y2/75% (mm/ml) | Z1/75% (mm/ml) | Z2/75% (mm/ml) |
|---|---|---|---|---|---|---|---|---|---|---|---|
| | 100% capacity (ml) | 75% capacity (ml) | Y1 | Y2 | Z1 | Z2 | | | | | |
| 1 | 430.0 | 325.0 | 5.0 | 131.5 | 15.0 | 49.5 | 0.015 | 0.405 | 0.046 | 0.152 |
| 2 | 406.7 | 305.0 | 4.0 | 136.5 | 17.5 | 51.0 | 0.013 | 0.448 | 0.057 | 0.167 |
| 3 | 360.0 | 270.0 | 1.0 | 133.5 | 9.0 | 48.5 | 0.004 | 0.494 | 0.033 | 0.180 |
| 4 | 443.3 | 335.0 | 13.5 | 103.5 | 14.0 | 55.0 | 0.040 | 0.309 | 0.042 | 0.164 |
| 5 | 383.3 | 290.0 | 12.0 | 139.0 | 25.5 | 51.0 | 0.041 | 0.479 | 0.088 | 0.176 |
| 6 | 346.7 | 260.0 | 3.0 | 132.0 | 10.5 | 50.5 | 0.012 | 0.508 | 0.040 | 0.194 |
| 7 | 441.7 | 330.0 | 10.5 | 129.0 | 15.5 | 54.5 | 0.032 | 0.391 | 0.047 | 0.165 |
| 8 | 391.7 | 295.0 | 3.0 | 144.5 | 15.0 | 50.0 | 0.010 | 0.490 | 0.051 | 0.169 |
| 9 | 346.7 | 260.0 | 1.5 | 147.0 | 13.0 | 49.5 | 0.006 | 0.565 | 0.050 | 0.190 |
| 10 | 366.6 | 270.0 | 21.7 | 130.3 | 19.3 | 50.0 | 0.080 | 0.482 | 0.071 | 0.185 |
| Salts Confidence Be | 310.0 | 235.0 | 8.0 | 126.5 | 5.5 | 46.0 | 0.034 | 0.538 | 0.023 | 0.196 |

FIG. 19

OSTOMY APPLIANCE

CROSS-REFERENCE TO RELATED APPLICATIONS

This application is a continuation of International Application No. PCT/GB2021/051336 filed Jun. 1, 2021 and claims the priority of foreign Application No. GB2008232.7 filed Jun. 2, 2020. The disclosures of which are hereby incorporated herein in their entirety.

TECHNICAL FIELD

The present disclosure relates to an ostomy appliance for managing effluent from a stoma.

BACKGROUND OF THE DISCLOSURE

There are many forms of ostomy appliance which try to provide a secure, comfortable fit for ostomates.

DE10 2014 104 737 describes an ostomy bag with a proximal film side and a distal film side, which enclose a bag cavity, an inlet opening for the entry of a stoma into the bag cavity being introduced in the proximal film side, and a valve being provided which has a valve bushing which forms an outlet opening from the bag cavity, and which has a valve plug with which the outlet opening can be closed. The valve bushing has a sealing section with a substantially cylindrical inner wall section, and the sealing section has a sealing collar which continues the cylindrical inner wall section in the direction of the bag cavity.

EU 001965120-0002, USD754848 and USD676550 show designs for ostomy appliances.

There remains a need for ostomy appliances with enhanced usability for ostomates, particularly in the areas of ease of use and discretion of use.

SUMMARY OF THE DISCLOSURE

In this specification, the term "stomal output" refers to any gases or fluids or solids produced by an ostomate that may be secreted from the stoma or that exit the stoma. The stomal output may comprise stomal gas, stomal liquid and stomal solids.

In this specification, the term "stoma" refers to an opening in the body. Generally the stoma is a surgical opening in the torso of the body. In some instances, the term "stoma" also refers to internal tissue, organs or portions thereof that are exposed by the opening. By way of non-limiting example, internal tissue may be selected from colon, ileum, small intestine, large intestine, jejunum, and duodenum, and combinations thereof. The internal tissue may be an end or a loop of a small or large intestine.

In this specification, the term "ostomate" refers to a subject that may have use of the ostomy appliance disclosed herein. While ostomate usually refers to a subject with a surgical opening, as used herein, "ostomate" may refer to a subject who has a stoma, regardless of whether the stoma was created by surgery or other means.

The term "user" may refer to an ostomate, or to another person assisting the ostomate, for example, with emptying of the stomal output from the cavity.

In this specification, the ostomy appliances disclosed herein may, for example, be used for managing a stoma created by an esophagostomy, a gastrostomy, a cholecystostomy, a choledochostomy, a cecostomy, a colostomy, a duodenostomy, an ileostomy, a jejunostomy, an appendicostomy, a tracheostomy, a urostomy, a nephrostomy, an ureterostomy, or a vesicostomy. The ostomy appliances disclosed herein may be used with additional devices including, but not limited to, a shunt, a catheter, a plug or a fecal management system.

Beneficially, the ostomy appliances of the present disclosure may permit an ostomate to increase the period of use of each ostomy appliance compared to prior art appliances. This may be achieved, for example, by providing an increased cavity volume for the ostomy appliance while maintaining ostomate discretion and comfort. Additionally or alternatively, this may also be achieved by providing means for draining the cavity of stomal output reliably and hygienically so as to increase an ostomate's confidence in reusing the ostomy appliance compared to some prior art appliances. Since the ostomate may be inclined to use each ostomy appliance of the present disclosure for longer, the total number of ostomy appliances used by the ostomate in a given time period may be reduced. This may produce an environmental benefit in reducing the amount of environmental waste produced.

In this specification locations and orientations of features may be described with reference to the ostomy appliance being "in use", "orientated as it would be in use" or similar. Such terms refer to the intended orientation of the ostomy appliance when it is adhered to a body of an ostomate with the ostomate in a standing position, irrespective of whether the ostomy appliance is currently performing such a use or the actual position of the ostomate. The terms "upper" and "lower" and related terms refer to the relative position of a part or portion of the ostomy appliance when orientated as it would be in use. For example, a section of the ostomy appliance may be referred to as an "upper" section of the ostomy appliance. In such an example, said section will be intended to be the uppermost section (in the vertical direction) of the ostomy appliance when attached to the body of a standing ostomate. However the reader skilled in the art will appreciate that before attachment to the ostomate said section may not always be the uppermost section and in addition when attached the section may not always be the uppermost section if the ostomate adopts a non-standing position, for example lying down.

The terms "left-hand" and "right-hand" and related terms refer to the ostomy appliance when viewed from the rear (for example, as shown in FIG. 1). Thus, as an illustrative example, a "left-hand" edge of the ostomy appliance will be towards a left-hand side of the ostomate in the situation where the ostomy appliance is attached to the front torso of the ostomate.

The terms "concave" and "convex" and related terms refer to shaping of features of the ostomy appliance when viewed from an exterior of the ostomy appliance. Thus, as an illustrative example, an ostomy wafer of circular shape would be considered to have a convexly shaped peripheral edge.

In this specification the terms "inner" and "outer" refer to the relative position of a part or portion of the ostomy appliance with reference to the body of an ostomate when the ostomy appliance is attached to the body. "Inner" refers to a position relatively closer to the body of the ostomate than a comparative position that is "outer". "Outer" refers to a position relatively further away from the body of the ostomate than a comparative position that is "inner".

In this specification the term "smoothly blends" and related terms refers to the smooth merging of two edges, lines or contours without abrupt changes in contour.

In this specification the term "peripheral region" refers to a portion situated on or towards an edge of the item being referred to.

The term "turned up" used herein may include folding or rolling of the components.

Ostomy appliances are commonly attached to the body by means of an ostomy wafer which includes an adhesive layer or layers. The ostomy wafer typically has an opening for the stoma sometimes referred to as a starter hole which may be cut to a required size by a user before attachment. The ostomy wafer typically comprises an adhesive layer on a body-facing side for adhering the ostomy wafer to the body of the ostomate. Typically, a release liner covers a body-facing side of the ostomy wafer that is removed by the user prior to fitting to the skin. In this specification, the term "ostomy wafer" may be used interchangeably with the terms "adapter," "wafer," "baseplate", or "layered adhesive wafer." In this specification, the term "ostomy wafer" includes ostomy wafers for a "two-piece appliance" and for a "one-piece appliance".

The ostomy wafer may have a generally circular shape. Alternatively the ostomy wafer may have a general oval or diamond shape, wherein a width, side-to-side, of the ostomy wafer is greater than the height, top-to-bottom.

In this specification a "two-piece appliance" refers to an appliance where the ostomy wafer forms part of a separate body fitment component that is attached by a releasable coupling to a pouch appliance. A two-piece appliance permits the body fitment component to be separated from the pouch appliance without damage, so that at least one of the parts continues to be functionally usable. For example, the body fitment component may remain in place on the body of the ostomate.

In this specification a "one-piece appliance" refers to an appliance where the ostomy wafer is permanently attached to the appliance, to the extent that the ostomy wafer cannot easily be separated without risk of damaging the appliance. A one-piece appliance is intended to be used as an integral unit.

Ostomy appliances are commonly configured as closed appliances or open appliances. In this specification a "closed appliance" refers to an appliance where it is not intended that stomal output is drained from the cavity. Thus, a closed appliance may typically be configured as a one-use, disposable and non-reusable appliance. In this specification an "open appliance" refers to an appliance where it is intended that stomal output is drained from the cavity. Thus, an open appliance may be configured as a reusable appliance, such that it can be reused and emptied multiple times whilst attached to the body, although this is not essential. In an open appliance the stomal output may be drained intermittently as instigated by an action of the ostomate or may be drained intermittently or continuously due to the cavity being fluidly connected to a drain, for example a night drain line.

In one aspect the present disclosure provides an ostomy appliance comprising an inner wall and an outer wall that define a cavity for containing a stomal output, the ostomy appliance having an upper section, a lower section and a waisted section that is located between the upper section and the lower section;

the inner wall comprising, within the upper section, an inlet for receiving the stomal output into the cavity;

the upper section having a maximum width (A) that is greater than a maximum width (B) of the lower section;

the waisted section having a minimum width (C) that is less than the maximum width (B) of the lower section; and the waisted section having a left-hand edge that is smoothly rounded and a right-hand edge that is smoothly rounded, and that both the left-hand edge and the right-hand edge smoothly blend, respectively, into left-hand edges and right-hand edges of the upper section and the lower section.

In embodiments, the cavity may comprise the upper section, the lower section and the waisted section located between the upper section and the lower section.

For example, the waisted section may smoothly merge with both the upper section and the lower section without abrupt changes in contour The ostomy appliance of the present disclosure may beneficially be used more discreetly since they have a reduced tendency to sag when filled and/or to distort or pucker in a manner that would tend to draw attention to the ostomy appliance when positioned beneath clothing.

Additionally or alternatively, in some embodiments the ostomy appliance may be a closed appliance and the appliance or the cavity may have a length (L) of 200 mm to 240 mm, optionally of 205 mm to 235 mm, optionally 208 mm or 230 mm. In some embodiments the ostomy appliance may be a closed appliance and the appliance or the cavity may have a length of 180 mm to 240 mm, optionally of 190 mm to 230 mm, optionally 194 mm, 217 mm or 224 mm.

Alternatively, the ostomy appliance may be an open appliance with a foldable drain extending from the cavity, and the appliance may have a length of 250 mm to 300 mm when a drain of the ostomy appliance is in an unfolded configuration, optionally a length of 290 mm. The ostomy appliance may be an open appliance with a foldable drain extending from the cavity, and may have a length of 230 mm to 300 mm when a drain of the ostomy appliance is in an unfolded configuration, optionally of 240 mm to 290 mm, optionally a length of 256 mm or 286 mm. With the drain in the folded configuration the open ostomy appliance may have a length of 180 mm to 240 mm, optionally of 190 mm to 230 mm, optionally 194 mm, 208 mm, 217 mm, 224 mm or 230 mm. Thus the cavity of an open appliance may have a length of 180 mm to 240 mm, optionally of 190 mm to 230 mm, optionally 194 mm, 208 mm, 217 mm, 224 mm or 230 mm Additionally or alternatively, in some embodiments the maximum width (A) of the upper section may be 135 mm to 150 mm, optionally 140 mm to 145 mm, optionally 142 mm.

Additionally or alternatively, in some embodiments the maximum width (B) of the lower section may be 130 mm to 145 mm, optionally 135 mm to 140 mm, optionally 137 mm to 139 mm.

Additionally or alternatively, in some embodiments the minimum width (C) of the waisted section may be 105 mm to 135 mm, optionally 110 mm to 130 mm, optionally 110 mm to 125 mm, optionally 115 mm to 130 mm, optionally 120 mm to 135 mm, optionally 115 mm to 120 mm, optionally 120 mm to 125 mm, optionally 125 mm to 130 mm, optionally 120 mm, optionally 129 mm, optionally 119 mm, optionally 109 mm.

Additionally or alternatively, in some embodiments the minimum width (C) of the waisted section may be 105 mm to 145 mm, optionally 110 mm to 140 mm, optionally 115 mm to 135 mm, optionally 120 mm to 130 mm, optionally 125 mm to 130 mm, optionally 127 or 128 mm.

Additionally or alternatively, in some embodiments the minimum width (C) of the waisted section may be 5 mm to 30 mm less than the maximum width (B) of the lower section, optionally 10 mm to 20 mm less than the maximum width (B) of the lower section, optionally 15 mm to 20 mm less than the maximum width (B) of the lower section.

Additionally or alternatively, in some embodiments the minimum width (C) of the waisted section may be 5 mm to 20 mm less than the maximum width (B) of the lower section, optionally 5 mm to 15 mm less than the maximum width (B) of the lower section, optionally 8 mm to 12 mm less than the maximum width (B) of the lower section, e.g. about 9 or 10 mm less than the maximum width (b) of the lower section.

Additionally or alternatively, in some embodiments the minimum width (C) of the waisted section may be 10 mm to 35 mm less than the maximum width (A) of the upper section, optionally 15 mm to 30 mm less than the maximum width (A) of the upper section, optionally 20 mm to 25 mm less than the maximum width (A) of the upper section.

Additionally or alternatively, in some embodiments the minimum width (C) of the waisted section may be 8 mm to 25 mm less than the maximum width (A) of the upper section, optionally 10 mm to 20 mm less than the maximum width (A) of the upper section, optionally 12 mm to 18 mm less than the maximum width (A) of the upper section, for example about 14 or 15 mm less than the maximum width (A) of the upper section.

Additionally or alternatively, in some embodiments the minimum width (C) of the waisted section may be 75% to 95% of the maximum width (B) of the lower section, optionally 80% to 90% of the maximum width (B) of the lower section, optionally 83% to 88% of the maximum width (B) of the lower section.

Additionally or alternatively, in some embodiments the minimum width (C) of the waisted section may be 75% to 97% of the maximum width (B) of the lower section, optionally 85% to 95% of the maximum width (B) of the lower section, optionally 90% to 94% of the maximum width (B) of the lower section, for example about 92% or 93% of the maximum width (b) of the lower section.

Additionally or alternatively, in some embodiments the minimum width (C) of the waisted section may be 73% to 92% of the maximum width (A) of the upper section, optionally 75% to 85% of the maximum width (A) of the upper section, optionally 80% to 85% of the maximum width (A) of the upper section.

Additionally or alternatively, in some embodiments the minimum width (C) of the waisted section may be 75% to 95% of the maximum width (A) of the upper section, optionally 80% to 92% of the maximum width (A) of the upper section, optionally 85% to 90% of the maximum width (A) of the upper section, for example about 89% of the maximum width (A) of the upper section.

Additionally or alternatively, in some embodiments a distance (D) of the minimum width (C) of the waisted section from the top edge of the ostomy appliance may be 90 mm to 125 mm, optionally 95 to 120 mm, optionally 105 to 115 mm, optionally 99 mm, optionally 109 mm, optionally 119 mm.

Additionally or alternatively, in some embodiments a distance (D) of the minimum width (C) of the waisted section from the top edge of the ostomy appliance may be 90 mm to 130 mm, optionally 95 mm to 125 mm, optionally 100 to 120 mm, optionally 102 mm, optionally 118 mm.

Additionally or alternatively, in some embodiments a distance (D) of the minimum width (C) of the waisted section from the top edge of the ostomy appliance may be 45% to 60% of a length (L) of the ostomy appliance (in the closed configuration if the appliance is drainable), optionally 47% to 57% of the length (L), optionally 50% to 55% of the length (L).

Additionally or alternatively, in some embodiments the left-hand edge and the right-hand edge of the waisted section may each be concavely-curved. The left-hand edge and the right-hand edge of the waisted section may each have a radius of curvature, or a blend of radii of curvature, wherein the or each radii of curvature may be 35 mm to 45 mm, optionally 40 mm. The left-hand edge and the right-hand edge of the waisted section may each have a radius of curvature, or a blend of radii of curvature, wherein the or each radii of curvature may be between 30 to 80 mm, optionally between 35 mm to 75 mm, optionally between 40 mm to 70 mm, optionally 60 mm. The left-hand edge and the right-hand edge of the waisted section may each have a radius of curvature, or a blend of radii of curvature, wherein the or each radii of curvature may be between 30 to 200 mm, optionally between 100 mm to 175 mm, optionally between 130 mm to 160 mm, optionally, for example, 150 mm.

Additionally or alternatively, in some embodiments the left-hand edge and the right-hand edge of the waisted section may be mirror images of each other.

Additionally or alternatively, in some embodiments the upper section may be generally rounded. The upper section may comprise a continuously curved edge that extends from the left-hand edge of the waisted section to the right-hand edge of the waisted section. The continuously curved edge of the upper section may be convexly curved. The continuously curved edge of the upper section may be absent any points of inflection or abrupt changes in contour. The continuously curved edge of the upper section may have a radius of curvature, or a blend of radii of curvature, wherein the or each radii of curvature may be 55 mm to 75 mm, optionally 60 to 73 mm.

Additionally or alternatively, in some embodiments a junction between the upper section and the waisted section may be demarcated by a single point of inflection between the left-hand edge of the upper section and the left-hand edge of the waisted section, and by a single point of inflection between the right-hand edge of the upper section and the right-hand edge of the waisted section. A junction between the lower section and the waisted section may be demarcated by a single point of inflection between the left-hand edge of the lower section and the left-hand edge of the waisted section, and by a single point of inflection between the right-hand edge of the lower section and the right-hand edge of the waisted section.

Additionally or alternatively, in some embodiments the lower section may be generally rounded. The lower section may comprise a continuously curved edge that extends from the left-hand edge of the waisted section to the right-hand edge of the waisted section. The continuously curved edge of the lower section may be convexly curved. The continuously curved edge of the lower section may be absent any points of inflection or abrupt changes in contour. The continuously curved edge of the lower section may have a radius of curvature, or a blend of radii of curvature, wherein the or each radii of curvature may be 45 mm to 70 mm, optionally 50 to 67 mm. Alternatively, the lower section may comprise a generally rounded portion and a generally rectangular portion, with the generally rectangular portion being adjacent the waisted section and generally rounded portion being distal the waisted section. The lower section may comprise a continuous lower edge that extends from the left-hand edge of the waisted section along a left-hand edge of the generally rectangular portion, around a continuously curved edge of the generally rounded portion and along a right-hand edge of the generally rectangular portion to the right-hand edge of the waisted section. The continuously curved edge of the generally rounded portion may be convexly curved. The continuously curved edge of the generally rounded portion may be absent any points of inflection or abrupt changes in contour. The continuously curved edge of the generally rounded portion may have a radius of curvature, or a blend of radii of curvature, wherein the or each radii of curvature may be 55 mm to 70 mm, optionally 67 mm. Alternatively, the lower section may comprise a drain aperture. The lower section may comprise a generally rounded portion and a drain portion that accommodates the drain aperture, with the generally rounded portion being adjacent the waisted section and the drain portion being distal the waisted section. The lower section may comprise a continuous left-hand edge that extends from the left-hand edge of the waisted section around a left-hand edge of the generally rounded portion and along a left-hand edge of the drain portion, and further comprises a continuous right-hand edge that extends from the right-hand edge of the waisted section around a right-hand edge of the generally rounded portion and along a right-hand edge of the drain portion. The left-hand edge and the right-hand edge of the generally rounded portion may each have a radius of curvature, or a blend of radii of curvature, wherein the or each radii of curvature may be 45 mm to 70 mm, optionally 50 to 67 mm.

Additionally or alternatively, in some embodiments the inner wall and the outer wall may be symmetrical about a vertical midline of the ostomy appliance.

Additionally or alternatively, in some embodiments the inner wall and the outer wall may be joined together by a single continuous edge seal. The ostomy appliance may be a closed appliance and the single continuous edge seal may form a closed peripheral seal. The single continuous edge seal may thus define the shape of the cavity. Alternatively, the ostomy appliance may be an open appliance and the single continuous edge seal may extend from a left-hand edge of a drain aperture to a right-hand edge of a drain aperture. The single continuous edge seal may thereby define both the shape of the cavity and the shape of the drain with which the cavity communicates. The single continuous edge seal maybe a weld, optionally a weld having a width of 3 mm to 5 mm, optionally of 4 mm. The single continuous edge seal may have a constant width around the perimeter of the ostomy appliance.

Additionally or alternatively, in some embodiments the inner wall and the outer wall may be formed from flexible sheet material. Optionally, the flexible sheet material of the inner wall and/or the outer wall may comprise a single layer or a laminate of a plurality of layers. Optionally, the flexible sheet material of the inner wall and/or the outer wall may comprise polyvinylidene chloride (PVDC) and/or ethylene-vinyl acetate (EVA). Optionally, the inner wall and/or the outer wall may have a thickness of 50 to 150 micrometres, optionally 75 to 100 micrometres.

Additionally or alternatively, in some embodiments the ostomy appliance may further comprise either an ostomy wafer that is located in register with the inlet of the inner wall, or a releasable coupling that is located in register with the inlet of the inner wall and that is configured for coupling with a body fitment component comprising an ostomy wafer. Additionally or alternatively, in some embodiments the ostomy wafer may be configured for a one-piece appliance or a two-piece appliance. Additionally or alternatively, in some embodiments the ostomy wafer may extend through the wafer aperture of the inner comfort layer. The ostomy wafer may have a general oval or diamond shape.

Additionally or alternatively, in some embodiments the ostomy appliance may further comprise at least one comfort layer overlying at least one of the inner wall and the outer wall. The ostomy appliance may comprise an inner comfort layer and/or an outer comfort layer.

Additionally or alternatively, in some embodiments the outer comfort layer may comprise a first part and a second part which may be joined to the outer wall so that the first part partially overlaps the second part in an overlap region. Optionally, the first part and the second part may be separable from each other in the overlap region to form a window opening for viewing the cavity. The overlap region may be angled to extend horizontally when the ostomy appliance is in use. Optionally, the first part and the second part of the outer comfort layer may be configured to slide over each other in the overlap region to accommodate expansion of the underlying outer wall. Optionally, the first part and the second part may be joined to each other at a first end and at a second end of the overlap region. Optionally, the first part and the second part may be welded to each other at the first end and at the second end of the overlap region, optionally as part of a peripheral weld of the ostomy appliance. Optionally, external edges of the one or more parts of the outer comfort layer are shaped and sized to be in register with the outer wall.

Additionally or alternatively, the inner comfort layer may comprise a single part or multiple parts. Optionally, the inner comfort layer may cover only a portion of the inner wall. However, preferably the inner comfort layer covers all of the inner wall (except for the inlet for receiving the stomal output into the cavity). Optionally, the inner comfort layer may be shaped and sized to be in register with the inner wall. Optionally, the inner comfort layer may be provided with a wafer aperture that is in register with the inlet of the inner wall to permit fluid connection of the inlet of the inner wall to an ostomy wafer.

Additionally or alternatively, in some embodiments the at least one comfort layer may be formed from a flexible sheet material. The material of the flexible sheet material may comprise one or more of polyester, nylon, viscose, polyurethane, polyethylene, polypropylene, polyvinylidene chloride (PVDC) and ethylene-vinyl acetate (EVA).

Additionally or alternatively, in some embodiments, the at least one comfort layer may comprise a laminate of two or more layers. Optionally, the at least one comfort layer may comprise at least one fabric layer and at least one film layer. The at least one film layer may be laminated to the at least one fabric layer, and optionally may be laminated to the at least one fabric layer over an entire area of the at least one comfort layer.

Additionally or alternatively, in some embodiments the at least one fabric layer may comprise a woven or a non-woven textile layer. The fabric layer may comprise polyester, nylon, viscose, polyethylene or polypropylene.

Additionally or alternatively, in some embodiments the at least one film layer may comprise polyurethane, polyvinylidene chloride (PVDC) or ethylene-vinyl acetate (EVA).

Additionally or alternatively, in some embodiments the at least one comfort layer may comprise a woven polyester layer. Additionally or alternatively, in some embodiments the at least one comfort layer may comprise ethylene-vinyl acetate (EVA) and/or polyvinylidene chloride (PVDC) and/or polyurethane layers.

Additionally or alternatively, in some embodiments the at least one comfort layer may have a thickness of 50 to 1000 micrometres, preferably 60 to 500 micrometres, more preferably 75 to 300 micrometres.

Additionally or alternatively, in some embodiments the cavity of the ostomy appliance may be configured with or without a drain. Thus, the ostomy appliance may be configured as an open or a closed appliance.

Additionally or alternatively, in some embodiments the inner wall and the outer wall may be joined together around a part or the whole of their peripheral edges. The joining may be by use of welding, adhesive or equivalent means. In the case of a closed appliance the peripheral join, for example a peripheral weld, may extend around a full perimeter of the inner wall and the outer wall to create a fluid-tight seal there between. Alternatively, in the case of an open appliance the peripheral join, for example a peripheral weld, may have one or more breaks that may demarcate drainage locations from the cavity.

Additionally or alternatively, in some embodiments the inner wall and the inner comfort layer may be joined together around their peripheral edges and/or the outer wall and the outer comfort layer may be joined together around their peripheral edges. The joining may be by use of welding, adhesive or equivalent means. A single joining operation may be used to join the inner comfort layer, the inner wall, the outer wall and the outer comfort layer together. For example a single weld may be used to join the four layers.

Additionally or alternatively, in some embodiments the cavity may be a single volume or may be sub-divided into two or more volumes. For example, the two or more volumes may be separated by partitions, wall members, filter elements, etc.

Additionally or alternatively, in some embodiments the cavity may be provided with a gas vent for venting of stomal gases from the cavity.

Additionally or alternatively, in some embodiments the ostomy appliance may be provided with an odour filter for reducing the release of unwanted odours from the cavity.

Additionally or alternatively, in some embodiments the ostomy appliance may comprise a separation wall for filtering gases and/or liquids from solid matter contained in the stomal output. For example, the inner wall may comprise a stomal inlet and the outer wall comprise a gas vent; and the separation wall may be provided between the inner and outer walls forming separate first and second chambers and comprising a liquid and gas permeable separation filter; wherein, in use: the first chamber is arranged to receive stomal output directed into the ostomy appliance via the stomal inlet; the separation filter is arranged to communicate, from the stomal output in the first chamber, stomal liquid and stomal gas to the second chamber; and the gas vent is arranged to allow the stomal gas to migrate from the second chamber to outside of the ostomy appliance.

In another example, the inner wall may comprise a stomal inlet for receiving stomal output and the outer wall may comprise a gas vent; the separation wall may comprise a liquid and gas permeable separation filter; and the ostomy appliance comprises a stomal output flow path for directing stomal output from the stomal inlet to the first chamber, a liquid flow path for directing stomal liquid from the stomal output in the first chamber to the second chamber via the separation filter and a gas flow path for stomal gas to migrate from the stomal output in the first chamber to the gas vent via the separation filter and second chamber.

In use stomal output may be received through the stomal inlet and communicated to the first chamber. The separation filter may filter stomal gas and stomal liquid from the stomal output and communicate the stomal gas and stomal liquid to the second chamber. The gas vent may release the stomal gas from the second chamber.

The present disclosure also provides a method of collecting stomal discharge in an ostomy appliance comprising use of an ostomy appliance as described herein. In one embodiment the method comprises attaching an ostomy wafer of a one-piece appliance as described herein over the stoma. In another embodiment the method comprises attaching an ostomy wafer of a body fitment component of a two-piece appliance as described herein over the stoma; and attaching a pouch appliance as described herein to the body fitment component. The pouch appliance may be attached to the body fitment component before or after the ostomy wafer has been attached over the stoma.

BRIEF DESCRIPTION OF THE DRAWINGS

One or more embodiments of the disclosure will now be described, by way of example only, with reference to the accompanying drawings in which:

FIG. 19 is a table of test results obtained from the testing illustrated in FIGS. 16 to 18.

DETAILED DESCRIPTION OF THE DISCLOSURE

Figure 1:
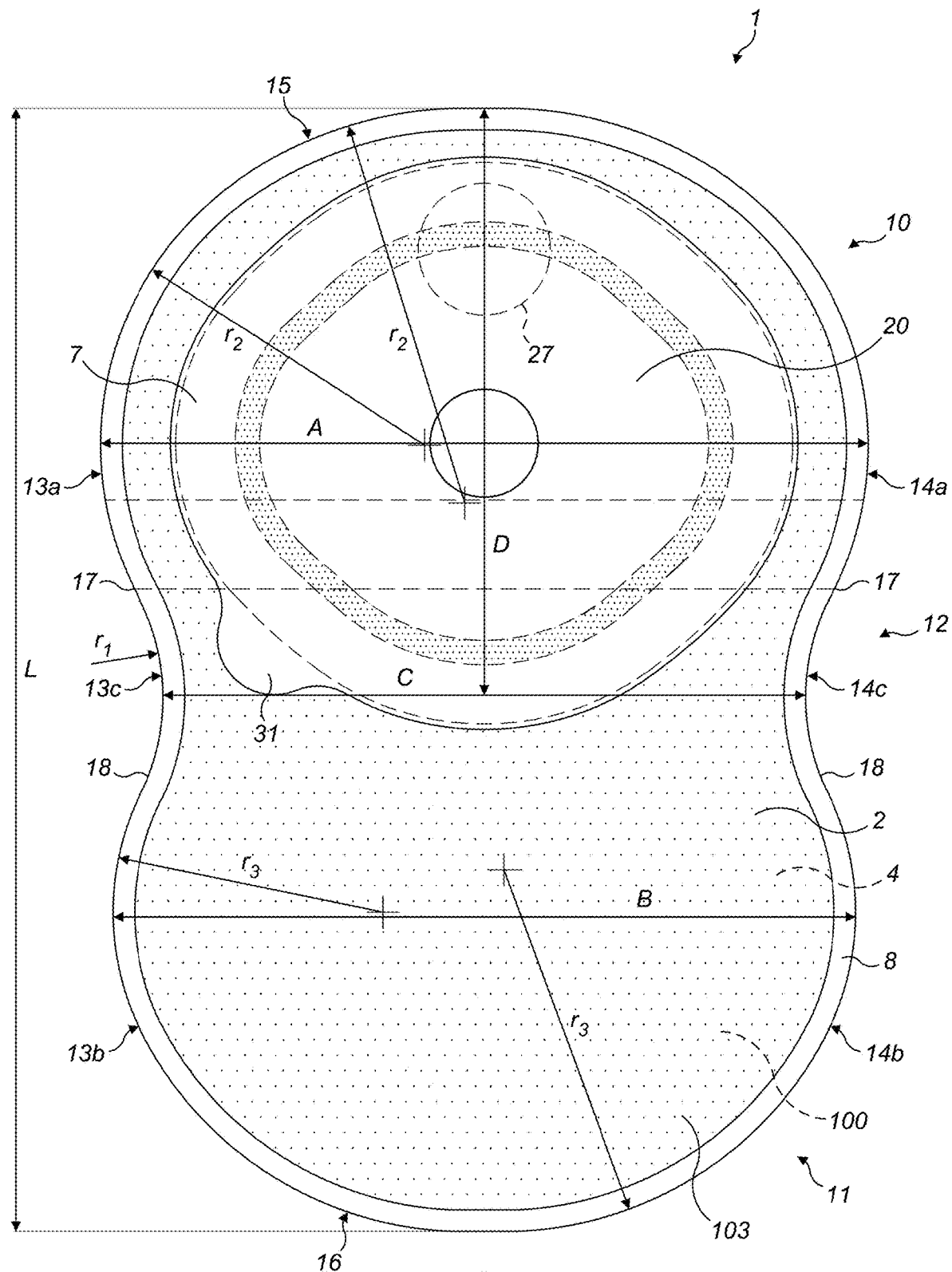
FIG. 1 is a rear view of an embodiment of ostomy appliance according to the present disclosure.

In the following description, the equivalent reference numerals are used in different embodiments to denote equivalent or similar features.

Unless defined otherwise, all technical and scientific terms used in this specification have the same meaning as is commonly understood by the reader skilled in the art to which the claimed subject matter belongs. It is to be understood that the foregoing summary of the disclosure and the following examples are exemplary and explanatory only and are not restrictive of any subject matter claimed.

The following description is directed to embodiments of the disclosure. The description of the embodiments is not meant to include all the possible embodiments of the disclosure that are claimed in the appended claims. Many modifications, improvements and equivalents which are not explicitly recited in the following embodiments may fall within the scope of the appended claims. Features described as part of one embodiment may be combined with features of one or more other embodiments unless the context clearly requires otherwise.

In this specification, the use of the singular includes the plural unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. For example, "about 5 mm" means "about 5 mm" and also "5 mm." Generally, the term "about" includes an amount that would be expected to be within experimental error. The term "about" includes values that are within 5% less to 5% greater of the value provided. For example, "about 30 mm" means "between 28.5 mm and 31.5 mm."

In this specification, unless the context demands otherwise, length and width and distance dimensions are measured on the ostomy appliance when flat and before receiving any stomal output.

Figure 2:
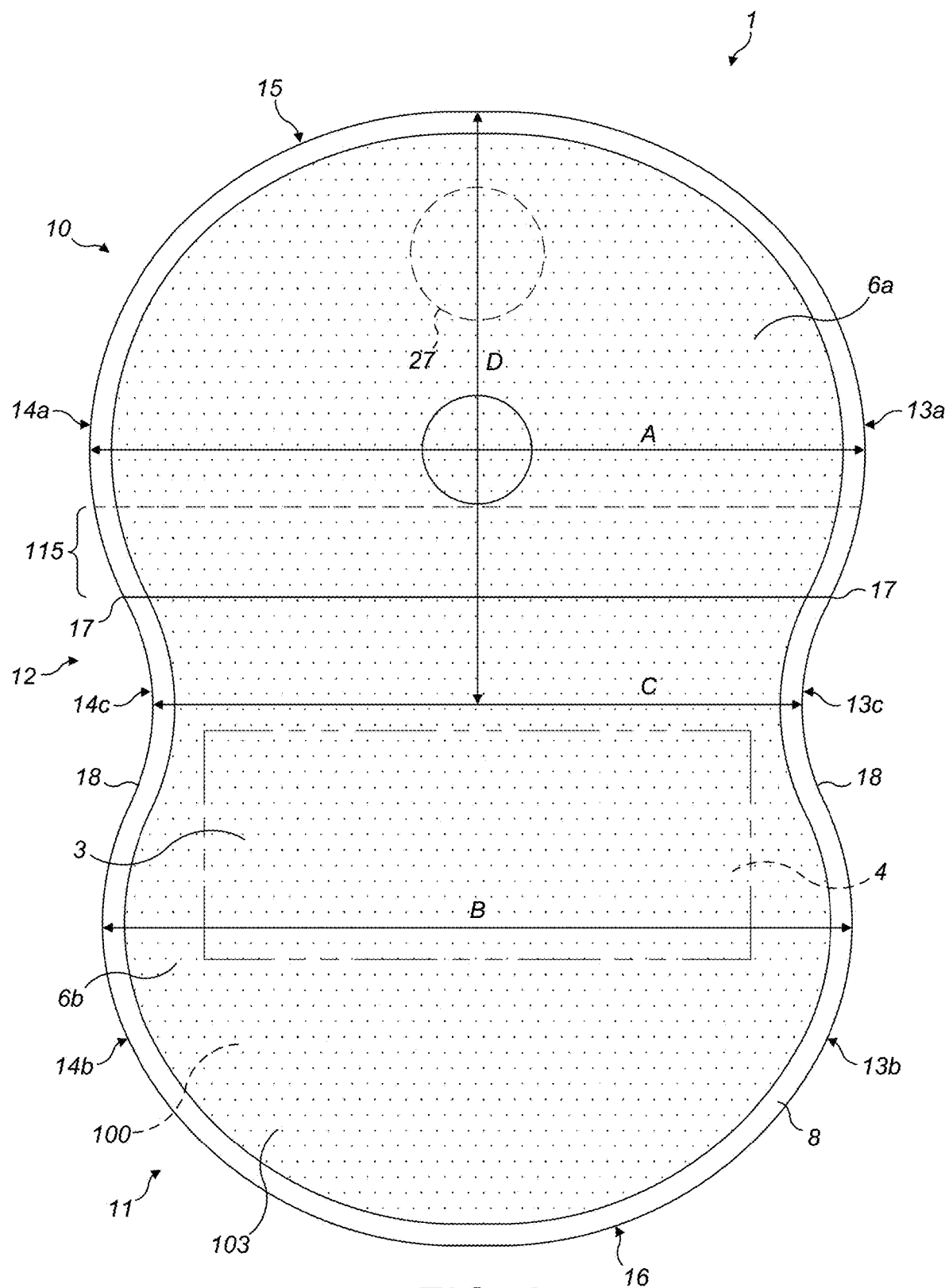
FIG. 2 is a front view of the ostomy appliance of FIG. 1.
Figure 3:
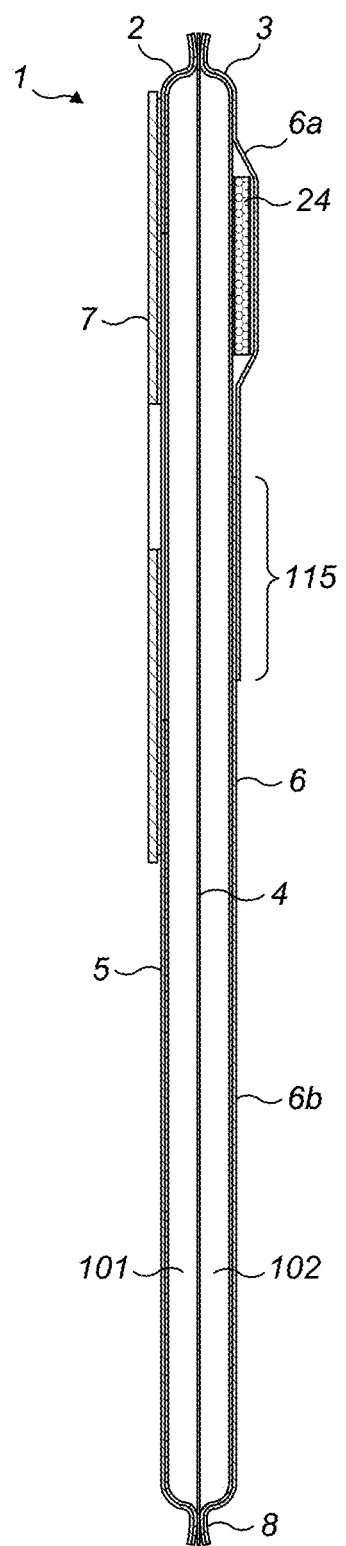
FIG. 3 is a cross-sectional side view of the ostomy appliance of FIG. 1.

A first example embodiment of an ostomy appliance 1 according to the present disclosure is shown in FIGS. 1 to 3. This example is a closed appliance.

As shown in FIGS. 1 to 3, the ostomy appliance 1 may generally comprise an inner wall 2, an outer wall 3, a separation wall 4, an inner comfort layer 5, an outer comfort layer 6 and an ostomy wafer 7. One or more of the separation wall 4, the inner comfort layer 5 and the outer comfort layer 6 may be omitted from the ostomy appliance if desired. For example, in some implementations an outer comfort layer 6 may not be required—for example when the ostomy appliance is to be used in a hospital or nursing home setting wherein easy observation of the contents of the cavity is desired. For example, in some implementations a separation wall 4 may not be required.

The ostomy appliance 1 of this example is a one-piece appliance wherein the ostomy wafer 7 is permanently attached to the ostomy appliance 1, to the extent that the ostomy wafer 7 cannot easily be separated without risk of damaging the ostomy appliance 1. However, the teachings of this disclosure may also be applied, with suitable alteration where necessary, to a two-piece appliance. For example, where the ostomy appliance 1 is a two-piece appliance the inner wall 2, the outer wall 3, the separation wall 4, the inner comfort layer 5 and the outer comfort layer 6 may together form a pouch appliance that in use may be coupled to a body fitment component that comprises the ostomy wafer 7.

The inner wall 2 and the outer wall 3 define a cavity for containing a stomal output. The inner wall 2 and the outer wall 3 may be joined together to define the cavity. The inner wall 2 and the outer wall 3 may be formed of flexible sheet material. The flexible sheet material of the inner wall 2 and the outer wall 3 may be formed of polyurethane, polyethylene (PE), polyvinylidene chloride (PVDC) and/or ethylene-vinyl acetate (EVA). The flexible sheet material may have a thickness of 50 to 150 micrometres, preferably 75 to 100 micrometres.

As seen in FIG. 1, the ostomy appliance 1 has an upper section 10, a lower section 11 and a waisted section 12 that is located between the upper section 10 and the lower section 11.

The upper section 10 has a maximum width, A. The lower section 11 has a maximum width, B. The waisted section 12 has a minimum width, C. The minimum width C is located at a distance, D from a top edge of the ostomy appliance as indicated on FIG. 1.

According to the present disclosure, the maximum width A of the upper section 10 is greater than the maximum width B of the lower section 11 and the minimum width C of the waisted section 12 is less than the maximum width B of the lower section 11.

The waisted section 12 has a left-hand edge 13c that is smoothly rounded and a right-hand edge 14c that is smoothly rounded. Both the left-hand edge 13c and the right-hand edge 14c smoothly blend, respectively, into left-hand edges 13a, 13b and right-hand edges 14a, 14b of the upper section 10 and the lower section 11 such that the waisted section 12 smoothly merges with both the upper section 10 and the lower section 11 without abrupt changes in contour, for example as shown in FIG. 1.

The ostomy appliance 1 may have a length, L, of 200 mm to 240 mm, optionally of 205 mm to 235 mm, optionally 208 mm or 230 mm. The length L may be measured from the top edge to the bottom edge of the ostomy appliance 1.

The maximum width, A of the upper section 10 may be 135 mm to 150 mm, optionally 140 mm to 145 mm, optionally 142 mm.

The maximum width, B of the lower section 11 may be 130 mm to 145 mm, optionally 135 mm to 140 mm, optionally 137 mm to 139 mm.

The minimum width, C of the waisted section 12 may be 105 mm to 135 mm, optionally 110 mm to 130 mm, optionally 110 mm to 125 mm, optionally 115 mm to 130 mm, optionally 120 mm to 135 mm, optionally 115 mm to 120 mm, optionally 120 mm to 125 mm, optionally 125 mm to 130 mm, optionally 129 mm, optionally 119 mm, optionally 109 mm.

Additionally or alternatively to the absolute magnitudes of the dimensions A, B and C, the minimum width, C of the waisted section 12 may be 5 mm to 30 mm less than the maximum width, B of the lower section 11, optionally 10 mm to 20 mm less than the maximum width, B of the lower section 11, optionally 15 mm to 20 mm less than the maximum width, B of the lower section 11.

Additionally or alternatively the minimum width, C of the waisted section 12 may be 10 mm to 35 mm less than the maximum width, A of the upper section 10, optionally 15 mm to 30 mm less than the maximum width, A of the upper section 10, optionally 20 mm to 25 mm less than the maximum width, A of the upper section 10.

Additionally or alternatively to the absolute magnitudes of the dimensions A, B and C, the minimum width, C of the waisted section 12 may be 75% to 95% of the maximum width, B of the lower section 11, optionally 80% to 90% of the maximum width, B of the lower section 11, optionally 83% to 88% of the maximum width, B of the lower section 11.

Additionally or alternatively the minimum width, C of the waisted section 12 may be 73% to 92% of the maximum width, A of the upper section 12, optionally 75% to 85% of the maximum width, A of the upper section 12, optionally 80% to 85% of the maximum width, A of the upper section 12.

Distance D, of the minimum width, C of the waisted section 12 from the top edge of the ostomy appliance may be 90 mm to 125 mm, optionally 95 to 120 mm, optionally 105 to 115 mm, optionally 99 mm, optionally 109 mm, optionally 119 mm.

Additionally or alternatively to the absolute magnitude of the dimension D, the distance, D of the minimum width, C of the waisted section 12 may be 45% to 60% of the length, L, optionally 47% to 57% of the length, L, optionally 50% to 55% of the length, L.

The left-hand edge 13*c* and the right-hand edge 14*c* of the waisted section 12 may each be concavely-curved. The left-hand edge 13*c* and the right-hand edge 14*c* of the waisted section 12 may be mirror images of each other. In some embodiments the left-hand edge 13*c* and the right-hand edge 14*c* of the waisted section 12 may each have a radius of curvature, $r_1$, or a blend of radii of curvature, wherein the or each radii of curvature is 35 mm to 45 mm, optionally 40 mm The upper section 10 may be generally rounded. The upper section 10 may comprise a continuously curved edge 15 that extends from the left-hand edge 13*c* of the waisted section 12 to the right-hand edge 14*c* of the waisted section 12. The continuously curved edge 15 of the upper section 10 may be convexly curved. The continuously curved edge 15 of the upper section 10 may be absent any points of inflection or abrupt changes in contour. The continuously curved edge 15 of the upper section 10 may incorporate part or all of the left-hand edge 13*a* and the right-hand edge 14*a* of the upper section 10. In some embodiments the continuously curved edge 15 of the upper section 10 may have a radius of curvature, $r_2$, or a blend of radii of curvature, wherein the or each radii of curvature is 55 mm to 75 mm, optionally 60 to 73 mm.

As can be seen in FIG. 1, a junction between the upper section 10 and the waisted section 12 may be demarcated by a single point of inflection 17 between the left-hand edge 13*a* of the upper section 10 and the left-hand edge 13*c* of the waisted section 12, and by a single point of inflection 17 between the right-hand edge 14*a* of the upper section 10 and the right-hand edge 14*c* of the waisted section 12. Similarly, a junction between the lower section 11 and the waisted section 12 may be demarcated by a single point of inflection 18 between the left-hand edge 13*b* of the lower section 11 and the left-hand edge 13*c* of the waisted section 12, and by a single point of inflection 18 between the right-hand edge 14*b* of the lower section 11 and the right-hand edge 14*c* of the waisted section 12.

The lower section 11 may be generally rounded. The lower section 11 may comprise a continuously curved edge 16 that extends from the left-hand edge 13*c* of the waisted section 12 to the right-hand edge 14*c* of the waisted section 12. The continuously curved edge 16 of the lower section 11 may be convexly curved. The continuously curved edge 16 of the lower section 11 may be absent any points of inflection or abrupt changes in contour. The continuously curved edge 16 of the lower section 11 may incorporate part or all of the left-hand edge 13*b* and the right-hand edge 14*b* of the lower section 11. In some embodiments the continuously curved edge 16 of the lower section 11 may have a radius of curvature, $r_3$, or a blend of radii of curvature, wherein the or each radii of curvature is 45 mm to 70 mm, optionally 50 to 67 mm.

The inner wall 2 and the outer wall 3 may be symmetrical about a vertical midline of the ostomy appliance 1.

The inner wall 2 may be provided with a stomal inlet 20 for receiving the stomal output into the cavity. The stomal inlet 20 may be an aperture that is cut out of the inner wall 2. The stomal inlet 20 may be located within the upper section 10 of the ostomy appliance 1.

The inner wall 2 and outer wall 3 may be joined together around their peripheral edges by use of welding, adhesive or equivalent means. The inner wall 2 and the outer wall 3 may be joined together by a single continuous edge seal 8. Welding is a preferred method of joining the inner wall 2 and the outer wall 3. The single continuous edge seal 8 may extend around a full perimeter of the inner wall 2 and the outer wall 3 to create a fluid-tight seal there between. Thus, the single continuous edge seal 8 may form a closed peripheral seal which may be a closed loop. The single continuous edge seal 8 may have a width of 3 mm to 5 mm, optionally of 4 mm. The single continuous edge seal 8 may be a weld. The weld may have a constant width around the perimeter of the ostomy appliance 1.

As shown in FIG. 3, the inner comfort layer 5 may overlie the inner wall 2 and the outer comfort layer 6 may overlie the outer wall 3.

The inner comfort layer 5 and the outer comfort layer 6 may be formed of a flexible sheet material. The flexible sheet material may comprise a fabric layer. The fabric layer may be a textile layer. The textile layer may be a woven or a non-woven textile layer. Examples of suitable materials include one or more of polyester, nylon, viscose, polyethylene and polypropylene.

The inner comfort layer 5 and the outer comfort layer 6 may comprise at least one fabric layer and at least one film layer. The at least one fabric layer may comprise a non-woven textile layer but is preferably a woven textile layer. The woven textile layer may comprise one or more of polyester, nylon, viscose, polyethylene and polypropylene. The film layer may comprise one or more of polyurethane, polyethylene (PE), polyvinylidene chloride (PVDC) and ethylene-vinyl acetate (EVA). The at least one film layer may be laminated to the at least one fabric layer, and optionally may be laminated to the at least one fabric layer over an entire area of the inner comfort layer 5 and the outer comfort layer 6.

The inner comfort layer 5 may overlie the inner wall 2. The inner comfort layer 5 may cover only a portion of the inner wall 2. However, it is preferred that the inner comfort layer 5 covers all of the inner wall 2 (except for the stomal inlet 20 of the inner wall 2).

The inner wall 2 and the inner comfort layer 5 may be joined together around their peripheral edges by use of welding, adhesive or equivalent means.

A peripheral weld may extend around the perimeter of the inner wall 2 and the inner comfort layer 5. The peripheral weld that joins the inner wall 2 with the inner comfort layer 5 may be the whole or a portion of the peripheral weld that joins the inner wall 2 and the outer wall 3.

The inner comfort layer 5 is preferably provided with a wafer aperture that is in register with the stomal inlet 20 of the inner wall 2.

The outer comfort layer 6 may overlie at least a portion of the outer wall 3. The outer wall 3 and the outer comfort layer 6 may be joined together around their peripheral edges by use of welding, adhesive or equivalent means. A peripheral weld may extend around the perimeter of the outer wall 3 and the outer comfort layer 6. The peripheral weld that joins the outer wall 3 with the outer comfort layer 6 may be the whole or a portion of the peripheral weld 8 that joins the inner wall 2 and the outer wall 3.

In some embodiments, the peripheral weld 8 may be one weld that joins together the inner comfort layer 5, the inner wall 2, the outer wall 3 and the outer comfort layer 6 (and the separation wall 4 if present).

The outer comfort layer 6 may comprise multiple parts. The external shape and dimensions of the multiple parts when taken together may be the same as that of the outer wall 3. For example, the outer comfort layer 6 may comprise an upper part 6a and a lower part 6b which may be joined to the outer wall 3 so that the upper part 6a partially overlaps the lower part 6b in an overlap region 115 as shown in FIG. 3. The upper part 6a and the lower part 6b may be separable from each other in the overlap region 115 to form a window opening for viewing the cavity. The overlap region 115 may extend horizontally when the ostomy appliance 1 is in use.

The ostomy wafer 7 may be located in register with the stomal inlet 20 of the inner wall 2. The ostomy wafer 7 may extend through the wafer aperture of the inner comfort layer 5. The ostomy wafer 7 may comprise an adhesive and a release liner 31. The ostomy wafer 7 may be mounted to the inner wall 2 by a suitable means, for example, by use of adhesive. The ostomy wafer 7 may have a generally circular shape. Alternatively the ostomy wafer 7 may have a general oval or diamond shape, wherein a width, side-to-side, of the ostomy wafer is greater than the height, top-to-bottom.

The ostomy appliance 1 may be provided with a gas vent for venting of stomal gases from the cavity. The ostomy appliance 1 may comprise a gas vent filter 24, which may be an odour filter, for example a charcoal or activated carbon filter, for reducing the release of unwanted odours from the cavity. As shown in FIG. 3, the gas vent filter 24 may form a part of the gas vent, which may comprise at least one gas vent aperture 27 located in the outer wall 3. The gas vent filter 24 may be covered by a filter cap and the gas vent filter 24 and/or filter cap may be located on the outer wall 3 over the at least one gas vent aperture 27. The at least one gas vent aperture 27 may permit the passage of gas from the cavity towards an exterior of the ostomy appliance through the gas vent filter 24 and filter cap (if present).

The gas vent may be located, in use, in the upper half or more preferably upper quarter of the ostomy appliance 1. In particular, the centre of the at least one gas vent aperture 27 may be located, in use, above the centre of the stomal inlet 20. The term "above" is intended to mean that the at least one gas vent aperture 27 is located in use uppermost of the stomal inlet 20 along a line parallel to the inner and outer walls 2, 3 when in a flat configuration.

As shown in FIG. 3, the separation wall 4 may be located between the inner wall 2 and the outer wall 3. The separation wall 4 may comprise a separation filter 100 for filtering stomal gases and/or stomal liquids from stomal solids contained in the stomal output. The separation filter 100 may thus prevent stomal solids from contacting the gas vent and clogging or otherwise impairing the functionality of the gas vent filter 24.

The cavity of the ostomy appliance 1 may be sub-divided into two volumes by the separation wall 4 to form first and second chambers 101, 102 as best illustrated in FIG. 3. The first chamber 101 may extend between the separation wall 4 and the inner wall 2 and the second chamber 102 may extend between the separation wall 4 and the outer wall 3. The first and second chambers 101, 102 may have substantially the same volume or they may have different volumes. The second chamber 102 may have a larger volume than the first chamber 101.

The separation wall 4 may be joined to the inner wall 2 and outer wall 3 at or adjacent to a part or the whole of their peripheral edges, preferably by use of welding, adhesive or equivalent means. Welding is a preferred method of joining and the peripheral weld that joins the inner wall 2, outer wall 3 and separation wall 4 may be the whole or a portion of the peripheral weld 8 that joins the inner wall 2 and the outer wall 3. As shown in FIGS. 1 and 2, the peripheral weld 8 may extend around a full perimeter of the inner wall 2, outer wall 3 and separation wall 4 to create a fluid-tight seal there between. Therefore, the joining of the separation wall 4 with the inner and outer walls 2, 3 may be such that the first and second chambers 101, 102 are sealed from one another other than via the separation filter 100.

The separation wall 4 may have the same external shape and dimensions as the inner wall 2 and the outer wall 3 so that the separation wall 4 extends entirely across all of the surface area of the inner and outer walls 2, 3. However, the separation wall 4 may instead be joined around at least part of its peripheral edge to only one of the inner and outer walls 2, 3. Therefore, the separation wall 4 may extend across at least 50% or at least 75% of the surface area of the inner and/or outer walls 2, 3. The separation wall 4 may at least partially extend across a lower half or lower quarter of the ostomy appliance 1 and may, as illustrated, extend entirely across the inner and outer walls 2, 3 and particularly between the peripheral weld 8 joining the inner and outer walls 2, 3.

The separation wall 4 may comprise a flexible sheet material, which may be formed of polyurethane, polyethylene (PE), polyvinylidene chloride (PVDC) and/or ethylene-vinyl acetate (EVA). The flexible sheet material of the separation wall 4 may have a thickness of 50 to 150 micrometres, preferably 75 to 100 micrometres. The separation wall 4 may comprise a hydrophobic and/or oleophobic coating applied to the flexible sheet material and/or the flexible sheet material may be hydrophobic and/or oleophobic.

The separation filter 100 may be liquid and gas permeable such that stomal liquid and stomal gas can migrate through the separation filter 100 to the second chamber 102 from the stomal output in the first chamber 101. The separation filter 100 may be substantially impermeable to the stomal solids in the stomal output such that the stomal solids substantially remain within the first chamber 101. Thus the separation filter 100 may effectively separate the stomal output into stomal solids in the first chamber 101 and stomal liquid and stomal gas in the second chamber 102.

The separation filter 100 may comprise at least one wall aperture 103 and preferably an array of wall apertures 103. The separation filter 100 may be otherwise substantially impermeable to gas and liquid other than through the at least one wall aperture 103. The at least one wall aperture 103 may be laser perforated in the separation wall 4. The maximum diameter of each wall aperture 103 may be in the range of from about 0.03 mm to about 0.8 mm, from about 0.06 mm to about 0.8 mm or from about 0.1 mm to about 0.4 mm inclusive. The spacing between adjacent wall apertures 103 in the array may be in the range of from about 0.8 mm to about 2.2 mm or from about 1 mm to about 2 mm. The wall apertures 103 of the array may comprise a stochastic and/or regular distribution. Preferably the entire array has a regular distribution as shown in FIGS. 1 and 2, although the array may have an entirely stochastic distribution or part of the array may comprise a stochastic distribution and part of the array may comprise a regular distribution.

The separation filter 100 and preferably array of wall apertures 103 may extend across at least 50%, at least 75% or at least 90% of the surface area of the separation wall 4. As illustrated in FIGS. 1 and 2, the array of wall apertures 103 may extend entirely across the separation wall 4. The separation filter 100 may extend across at least the lower half or lower quarter of the separation wall 4 and/or inner and outer walls 2, 3. The separation filter 100 may extend across at least the upper half or upper quarter of the separation wall 4 and/or inner and outer walls 2, 3. The separation filter 100 may not extend into the region of the peripheral weld 8 and, prior to assembly, the separation wall 4 may comprise a peripheral region without any wall apertures 103.

Figure 4:
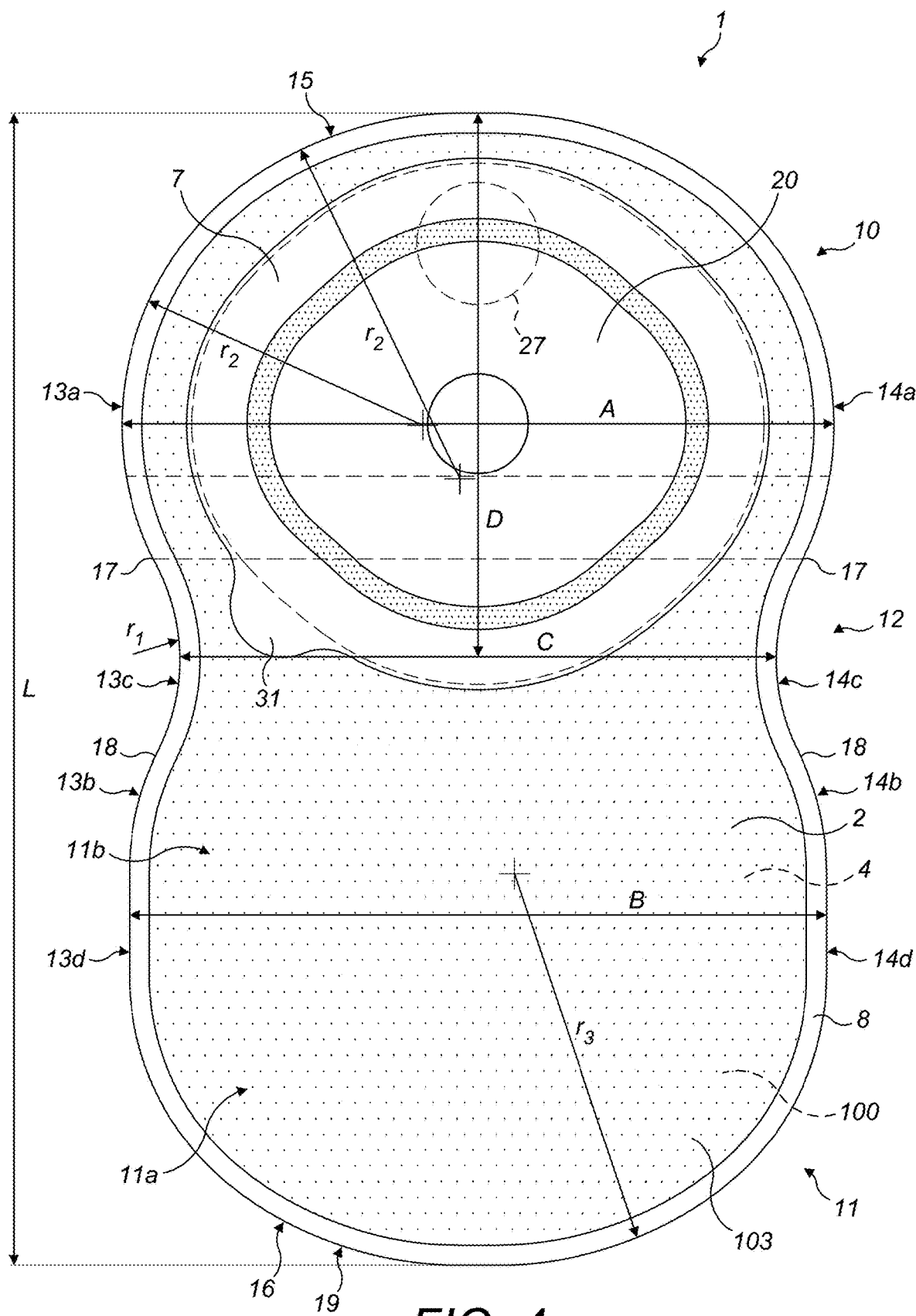
FIG. 4 is a rear view of another embodiment of ostomy appliance according to the present disclosure.
Figure 5:
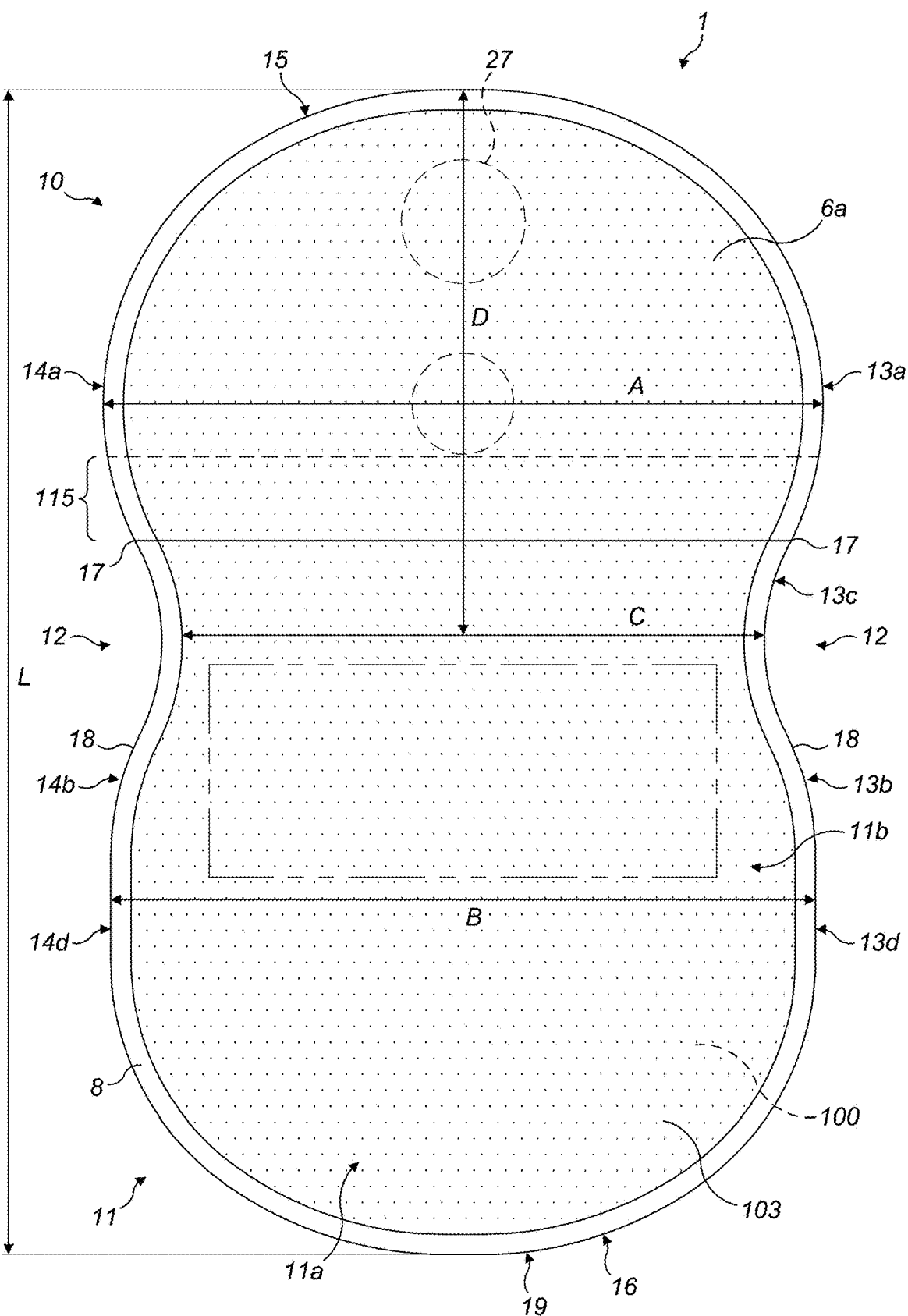
FIG. 5 is a front view of the ostomy appliance of FIG. 4.
Figure 6:
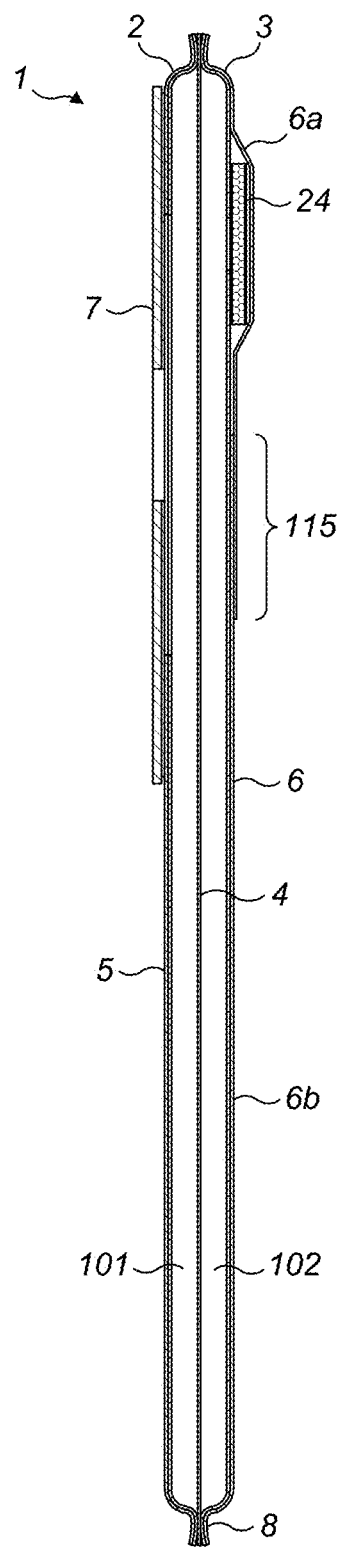
FIG. 6 is a cross-sectional side view of the ostomy appliance of FIG. 4.

A second example embodiment of an ostomy appliance 1 according to the present disclosure is shown in FIGS. 4 to 6. Like reference numerals have been used for like features. Only those features that differ in this embodiment compared to the previous embodiment will be described in detail in the following description. For features that are common to one or more embodiments, reference should be made to the description as a whole.

As in the above embodiment the maximum width, A of the upper section 10 is greater than the maximum width, B of the lower section 11 and the minimum width, C of the waisted section 12 is less than the maximum width, B, of the lower section 11. The absolute and/or relative dimensions of A, B, C and D may be the same as in the first example embodiment.

Also, as above, the waisted section 12 has a left-hand edge 13c that is smoothly rounded and a right-hand edge 14c that is smoothly rounded. Both the left-hand edge 13c and the right-hand edge 14c smoothly blend, respectively, into left-hand edges 13a, 13b and right-hand edges 14a, 14b of the upper section 10 and the lower section 11 such that the waisted section 12 smoothly merges with both the upper section 10 and the lower section 11 without abrupt changes in contour, for example as shown in FIG. 4.

Compared to the first example embodiment, the lower section 11 is shaped differently, and in particular is more elongated. As can be seen in FIG. 4, the lower section 11 may comprise a generally rounded portion 11a and a generally rectangular portion 11b, with the generally rectangular portion 11b being adjacent the waisted section 12 and the generally rounded portion 11a being distal the waisted section 12.

The location of the maximum width, B, of the lower section 11 may be within the rectangular portion 11b, i.e. the width of the rectangular portion 11b may be B.

As can be seen in FIG. 4, a junction between the upper section 10 and the waisted section 12 may be demarcated by a single point of inflection 17 between the left-hand edge 13a of the upper section 10 and the left-hand edge 13c of the waisted section 12, and by a single point of inflection 17 between the right-hand edge 14a of the upper section 10 and the right-hand edge 14c of the waisted section 12. Similarly, a junction between the lower section 11 and the waisted section 12 may be demarcated by a single point of inflection 18 between the left-hand edge 13b of the lower section 11 and the left-hand edge 13c of the waisted section 12, and by a single point of inflection 18 between the right-hand edge 14b of the lower section 11 and the right-hand edge 14c of the waisted section 12.

The lower section 11 may comprise a continuously curved edge 16 which may extend from the left-hand edge 13c of the waisted section 12 along a left-hand edge 13d of the generally rectangular portion 11b, around a continuously curved edge 19 of the generally rounded portion 11a and along a right-hand edge 14d of the generally rectangular portion 11b to the right-hand edge 14c of the waisted section 12. The continuously curved edge 16 of the lower section 11 may incorporate part or all of the left-hand edge 13b and the right-hand edge 14b of the lower section 11. The continuously curved edge 19 of the generally rounded portion 11a may be convexly curved. The continuously curved edge 19 of the generally rounded portion 11a may be absent any points of inflection or abrupt changes in contour. In some embodiments the continuously curved edge 19 of the generally rounded portion 11a has a radius of curvature, $r_3$, or a blend of radii of curvature, wherein the or each radii of curvature is 55 mm to 70 mm, optionally 67 mm.

In other respects the second example embodiment is the same as the first example embodiment described above.

A third example embodiment of an ostomy appliance 1 according to the present disclosure is shown in FIGS. 7 to 10. Like reference numerals have been used for like features. Only those features that differ in this embodiment compared to the previous embodiments will be described in detail in the following description. For features that are common to one or more embodiments, reference should be made to the description as a whole.

As in the above example embodiments the maximum width, A of the upper section 10 is greater than the maximum width, B of the lower section 11 and the minimum width, C of the waisted section 12 is less than the maximum width, B of the lower section 11. The absolute and/or relative dimensions of A, B, C and D may be the same as in the first example embodiment.

Figure 7:
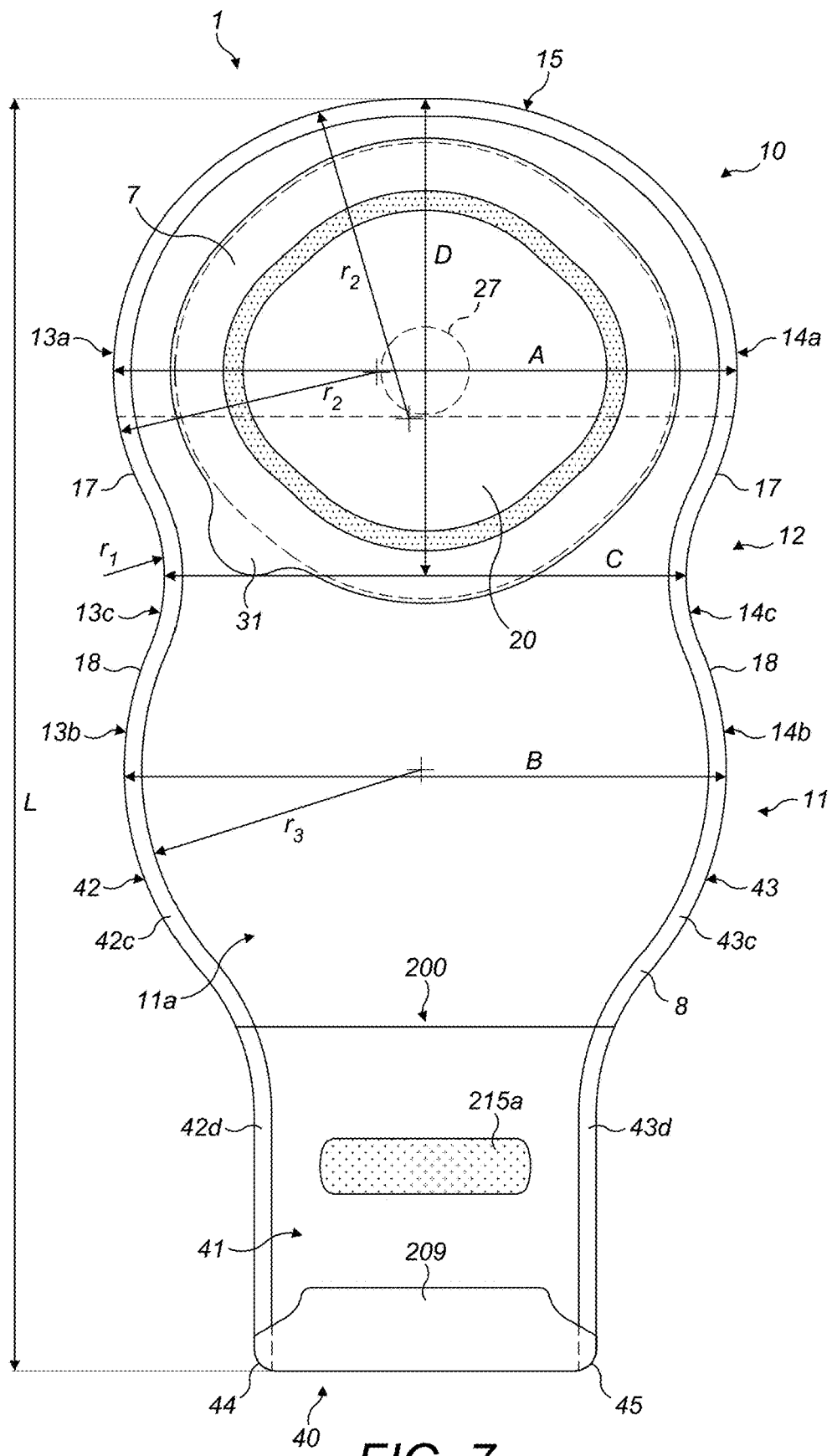
FIG. 7 is a rear view of another embodiment of ostomy appliance according to the present disclosure.

The ostomy appliance 1 of this embodiment is an open appliance and may have a length, L, of 230 mm to 300 mm when a drain of the ostomy appliance is in an unfolded configuration as shown in FIG. 7, optionally a length, L, of 256 mm, 286 mm or 290 mm.

Also, as above, the waisted section 12 has a left-hand edge 13c that is smoothly rounded and a right-hand edge 14c that is smoothly rounded. Both the left-hand edge 13c and the right-hand edge 14c smoothly blend, respectively, into left-hand edges 13a, 13b and right-hand edges 14a, 14b of the upper section 10 and the lower section 11 such that the waisted section 12 smoothly merges with both the upper section 10 and the lower section 11 without abrupt changes in contour, for example as shown in FIG. 7.

As can be seen in FIG. 7, a junction between the upper section 10 and the waisted section 12 may be demarcated by a single point of inflection 17 between the left-hand edge 13a of the upper section 10 and the left-hand edge 13c of the waisted section 12, and by a single point of inflection 17 between the right-hand edge 14a of the upper section 10 and the right-hand edge 14c of the waisted section 12. Similarly, a junction between the lower section 11 and the waisted section 12 may be demarcated by a single point of inflection 18 between the left-hand edge 13b of the lower section 11 and the left-hand edge 13c of the waisted section 12, and by a single point of inflection 18 between the right-hand edge 14b of the lower section 11 and the right-hand edge 14c of the waisted section 12.

Compared to the first example embodiment, the lower section 11 is shaped differently so as to accommodate a drain. The lower section 11 may comprise a drain aperture 40. The drain aperture 40 may be an unsealed portion of the perimeter of the ostomy appliance 1, e.g. a region of the perimeter of the inner wall 2 and outer wall 3 which are not sealed to each other.

The lower section 11 may comprise a generally rounded portion 11a and a drain portion 41 that accommodates the drain aperture 40, with the generally rounded portion 11a being adjacent the waisted section 12 and the drain portion 41 being distal the waisted section 12. The drain portion 41 may have a generally rectangular shape in whole or in part.

The lower section 11 may comprise a continuous left-hand edge 42 that may extend from the left-hand edge 13c of the waisted section 12 to a left-hand vertex 44 of the drain aperture 40. The left-hand edge 42 may extend around a continuously curved left-hand edge 42c of the generally rounded portion 11a and along a left-hand edge 42d of the drain portion 41. Similarly, the lower section 11 may comprise a continuous right-hand edge 43 that may extend from the right-hand edge 14c of the waisted section 12 to a right-hand vertex 45 of the drain aperture 40. The right-hand edge 43 may extend around a continuously curved right-hand edge 43c of the generally rounded portion 11a and along a right-hand edge 43d of the drain portion 41.

The continuously curved left-hand edge 42 of the lower section 11 may incorporate part or all of the left-hand edge 13b of the lower section 11 and the continuously curved right-hand edge 43 of the lower section 11 may incorporate part or all of the right-hand edge 14b of the lower section 11.

The continuously curved left-hand edge 42c of the generally rounded portion 11a and the continuously curved right-hand edge 43c of the generally rounded portion 11a may be convexly curved. In some embodiments the continuously curved left-hand edge 42c of the generally rounded portion 11a and the continuously curved right-hand edge 43c of the generally rounded portion 11a may each have a radius of curvature, $r_3$, or a blend of radii of curvature, wherein the or each radii of curvature is 45 mm to 70 mm, optionally 50 to 67 mm.

The left-hand edge 42d of the drain portion 41 and the right-hand edge 43d of the drain portion 41 may be parallel to one another along at least a part of their lengths, optionally a distal-part of their lengths. The left-hand edge 42d and the right-hand edge 43d of the drain portion 41 may each comprise a concavely-curved section in the transition between the generally rounded portion 11a and the drain portion 41.

A single continuous edge seal 8 may extend from the left-hand vertex 44 of the drain aperture 40 to the right-hand vertex 45 of the drain aperture 40.

The drain portion 41 may define an elongate drain passage that extends from the cavity of the ostomy appliance 1 to the drain aperture 40 located at a lower end of the drain portion 41 as shown in FIG. 7.

The drain portion 41 may be integral with a remainder of the lower section 11. In particular, the inner wall 2 and the outer wall 3 may each be a single piece of material that includes the upper section 10, the waisted section 12 and lower section 11 (including the drain portion 41) as most clearly shown in the exploded view of FIG. 10.

As in the above example embodiments, an inner comfort layer 5 and an outer comfort layer 6 may be provided. However, as most clearly shown in FIG. 10, the inner comfort layer 5 and outer comfort layer 6 may not cover the drain portion 41 of the inner wall 2 and the outer wall 3.

Communication between the cavity and the elongate drain passage may be via a drain inlet 200 that may be defined as the point of transition between the cavity and the drain portion 41. The drain inlet 200 may function to allow passage of stomal output from the cavity into the drain portion 41 when the drain portion 41 is in an extended configuration, e.g. an unrolled configuration as shown in FIG. 7. The drain aperture 40 may allow outflow of the stomal output from the drain portion 41 when the drain portion 41 is in the extended configuration.

The separation wall 4 may be joined to the inner wall 2 and outer wall 3 at or adjacent to a part or the whole of the peripheral edges of the upper section 10, waisted section 12 and the generally rounded portion 11a of the lower section 11. Welding is a preferred method of joining and the peripheral weld that joins the inner wall 2, outer wall 3 and separation wall 4 may be the whole or a portion of the peripheral weld 8 that joins the inner wall 2 and the outer wall 3. A lower portion of the separation wall 4 may be aligned with the drain inlet 200. A lowermost edge 4a of the separation wall 4 is left unattached from the inner wall 2 and the outer wall 3. In this way the folding of the drain portion 41 when moved into a rolled-up configuration folds the inner wall 2, outer wall 3 and the separation wall 4 such that the first and second chambers 101, 102 are sealed from each other (other than via the separation filter 100). However, the lowermost edge being unattached permits stomal output from the first chamber 101 and the second chamber 102 to enter the drain portion 41 when the drain portion 41 is in an extended configuration.

The drain portion 41 may be moved between an extended configuration, in which the drain aperture 40 is open, and a rolled-up configuration, in which the drain aperture 40 is closed off to hinder or prevent outflow of the stomal output. For example, the drain portion 41 may be configured to be folded or otherwise turned up on itself to close off the drain aperture 40.

The ostomy appliance 1 may be provided, by way of example, with features to assist in the folding or rolling-up of the drain portion 41 as will be described below.

In some embodiments, the drain portion 41 may be folded into a plurality of segments having approximately equal segment lengths and separated by folds. The drain portion 41 may therefore be successively folded one or more times such that the segments overlie each other. The drain portion 41 may be configured to be folded to form a plurality of folds across the width of the drain portion 41 to inhibit and preferably prevent passage of stomal output out of the drain aperture 40. For example, the segments and fold lines may have appropriate lengths and locations respectively such that the drain portion 41 can be folded or rolled repeatedly in the same sense, folding forwards and upwards towards an upper end of the drain portion 41 with each fold. The folds may be generally perpendicular to an elongate axis of the drain portion 41 and extend across the whole width of the drain portion 41 to close off the drain passage at each fold location.

In some embodiments, one or more pursing strips 209, 210 may be provided on the drain portion 41. The pursing strips 209, 210 may function to both provide localised rigidity to the drain portion 41 and also to define the locations and orientations of the segments and folds of the drain portion 41. The pursing strips 209, 210 may comprise strips of material attached drain portion 41. The pursing strips 209, 210 may be formed from a material, preferably a flexible material, having a higher rigidity than the material of the drain portion 41 and having some resilience such that once attached to the drain portion 41 the pursing strips 209, 210 can each be squeezed laterally to arch the pursing strip (and therefore the attached material of the drain portion 41) and thereby open the elongate drain passage. The pursing strips 209, 210 may be formed from polystyrene. As shown in FIGS. 7 to 10, a first pursing strip 209 may be attached to the inner wall 2 of the drain portion 41 and may be attached at a distal end of the inner wall 2 at or adjacent the drain aperture 40. A second pursing strip 210 may be attached to the outer wall 3 of the drain portion 41. As shown in FIG. 9, a longitudinal gap may be provided between an upper edge of the first pursing strip 209 and a lower edge of the second pursing strip 210. The longitudinal gap may define the location of a first fold of the drain portion 41. Each of the pursing strips 209, 210 may extend the same distance along a length of the drain portion 41.

A first fastening element 215a may be arranged on the inner wall 2. A second fastening element 215b may be arranged on, or depend from, the outer wall 3. The first closure element 215a and the second closure element 215b may comprise any suitable fastener elements, for example hook-and-loop type fastener elements. The first fastening element 215a may be located on the drain portion 41 upwards of the location of the second pursing strip 210 as shown in FIG. 9. A longitudinal gap may be provided between an upper edge of the second pursing strip 210 and a lower edge of the first fastening element 215a. The longitudinal gap may define the location of a second fold of the drain portion 41.

Figure 8:
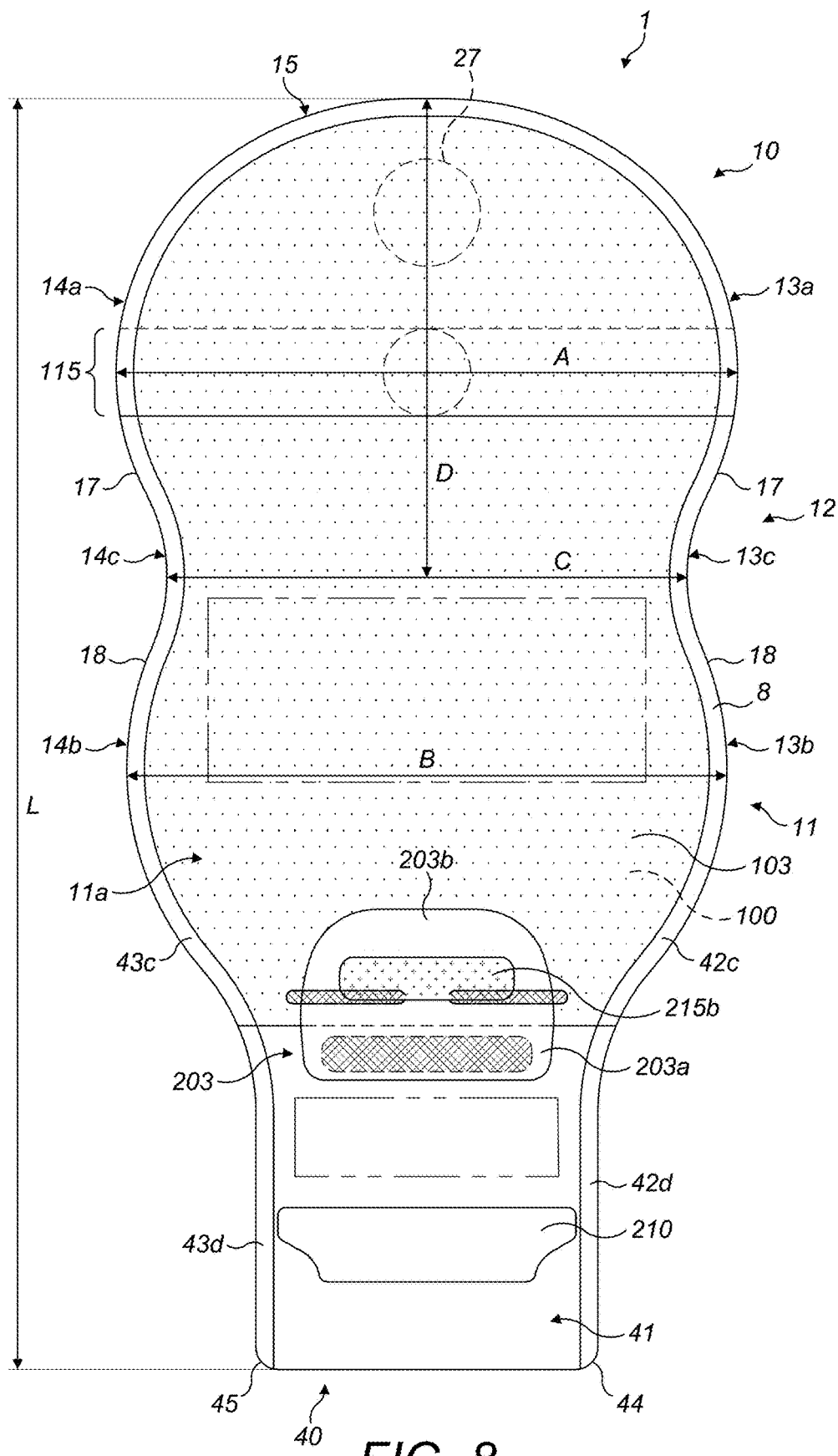
FIG. 8 is a front view of the ostomy appliance of FIG. 7.
Figure 9:
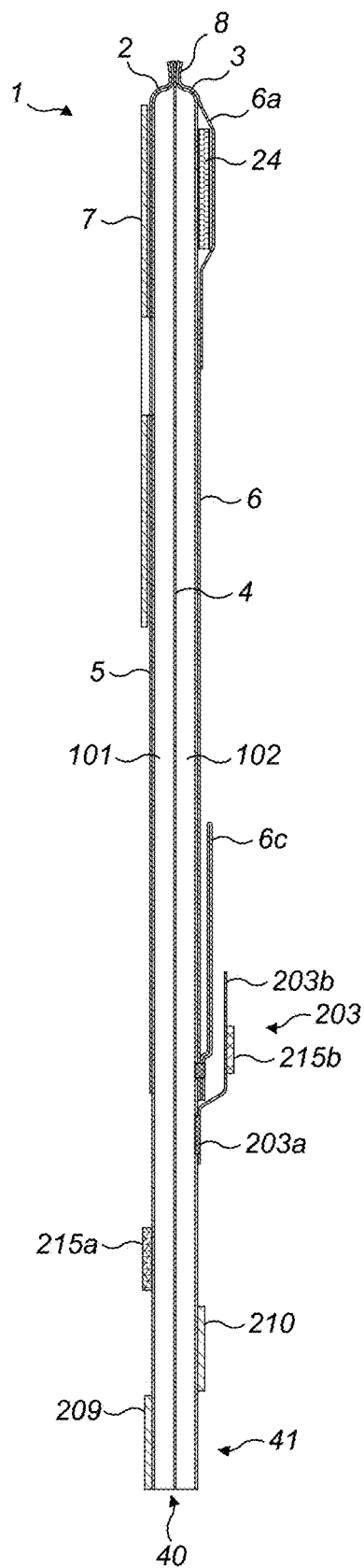
FIG. 9 is a cross-sectional side view of the ostomy appliance of FIG. 7.

As shown in FIG. 8, the second fastening element 215b may be provided on a flap 203 that is itself mounted or affixed to the outer wall 3. The flap 203 may comprise a first flange 203a and a second flange 203b. The second flange 203b may extend from the first flange 203a, the first flange 203a and the second flange 203b may be one integral piece and may meet at a fold line such that the second flange 203b is rotatable about the fold line. The first flange 203a may be attached to the outer wall 3 while the second flange 203b hangs free of the outer wall 3. The attachment of the first flange 203a may be formed using an adhesive or by welding. The second fastening element 215b may be located on the second flange 203b. The flap 203 may be formed from a flexible sheet material. The flexible sheet material may be more rigid than the flexible sheet material of the inner wall 2 and outer wall 3.

The flap 203 may be located on the drain portion 41 upwards of the location of the first fastening element 215a as shown in FIG. 9. A longitudinal gap may be provided between an upper edge of the first fastening element 215a and a lower edge of the flap 203. The longitudinal gap may define the location of a third fold of the drain portion 41.

Rolling-up of the drain portion 41 may be carried out as follows. First, the user or ostomate may fold the distal end of the drain portion 41 outwards and upwards about the first fold line to locate the first pursing strip 209 over the second pursing strip 210. Secondly, the drain portion 41 and the pursing strips 209, 210 may be folded again, in the same sense—outwards and upwards, about the second fold line and then the third fold line such that the folded and stacked first pursing strip 209, second pursing strip 210 and first fastening element 215a are located to overlie the first flange 203a of the flap 203 with the first fastening element 215a being exposed. Finally the second flange 203b of the flap 203 can be folded down to secure together the first fastening element 215a and the second fastening element 215b.

The drain portion 41 can be unrolled by reversing the above procedure.

Figure 10:
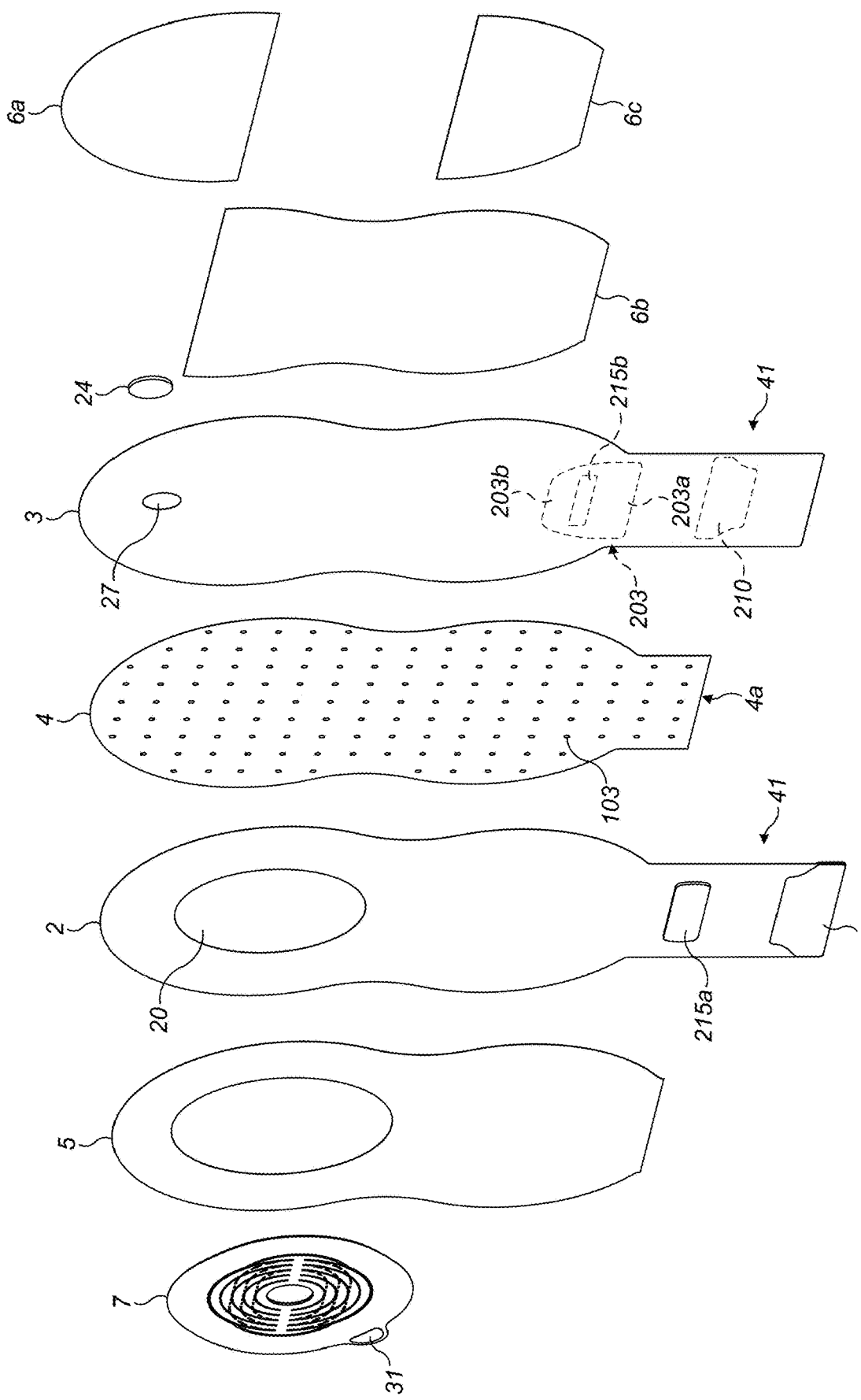
FIG. 10 is an exploded perspective view of the ostomy appliance of FIG. 7.

Optionally, the ostomy appliance 1 may be provided with a pocket 6c, as shown in FIG. 10. The pocket 6c may be formed from the same type of material as the outer comfort layer 6. The pocket 6c may be shaped and sized to cover a lower portion of the lower part 6b of the outer comfort layer 6. The lateral edges and lower edge of the pocket 6c may be joined to the outer comfort layer 6, for example by welding. The upper edge of the pocket 6c is left unsealed to form an upper mouth of the pocket 6c.

When the drain portion 41 is in the rolled-up configuration the length of the ostomy appliance 1 may be reduced by folding the lower section 11 outwards and upwards and tucking the distal end of the ostomy appliance 1 into the upper mouth of the pocket 6c. This may be particularly appropriate when the ostomy appliance 1 is empty or only contains a small volume of stomal output. As the cavity is filled the ostomate may untuck the lower section 11 from the pocket 6c.

It will be appreciated that the configuration of the drain portion 41 of this example is provided merely as one example of a drain. Other configurations of drain may be used for an open appliance according to the present disclosure.

Figure 11A:
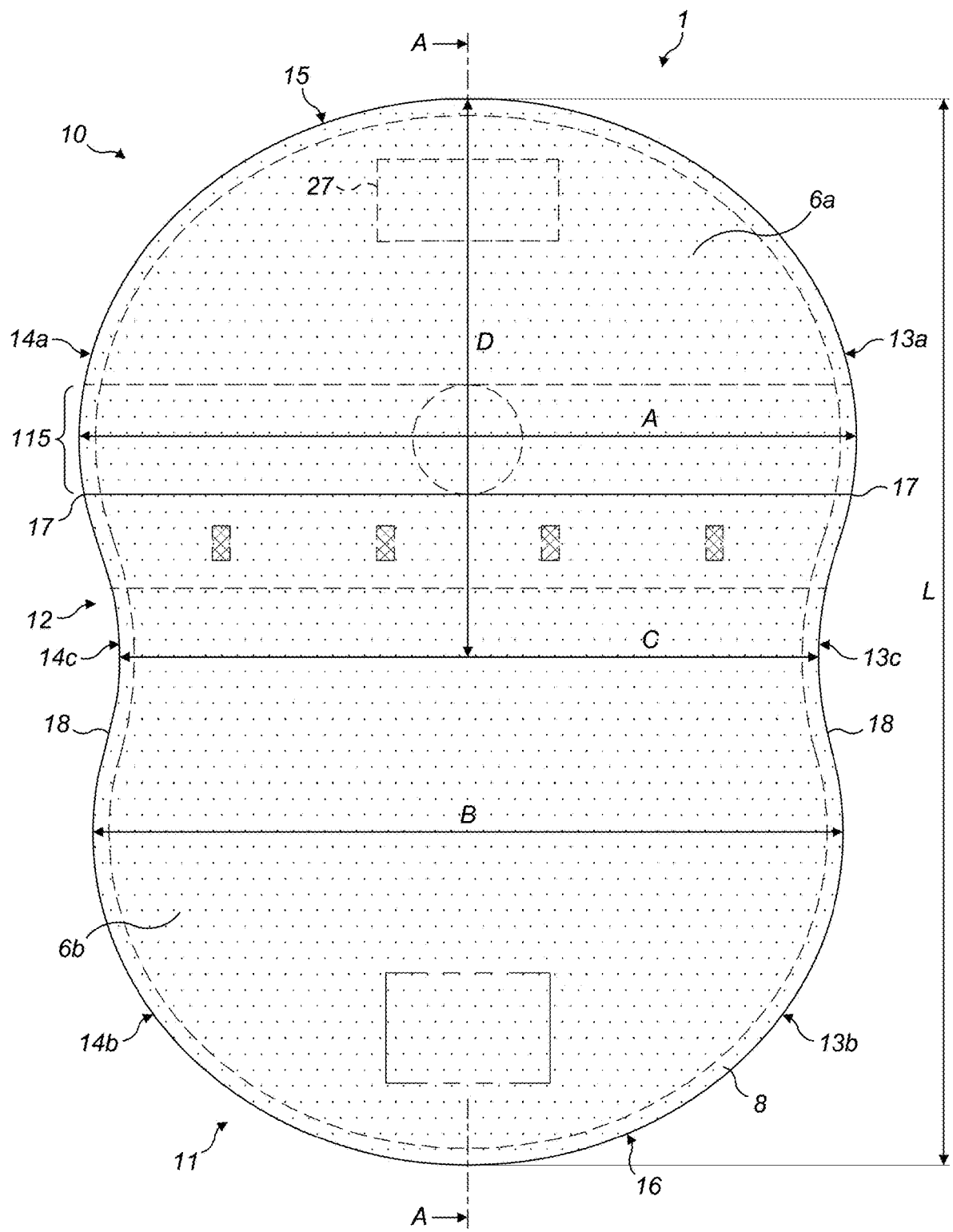
FIGS. 11A to 11C are front views, cross-sectional side views, and rear views respectively of another embodiment of an ostomy appliance according to the present disclosure.
Figure 11B:
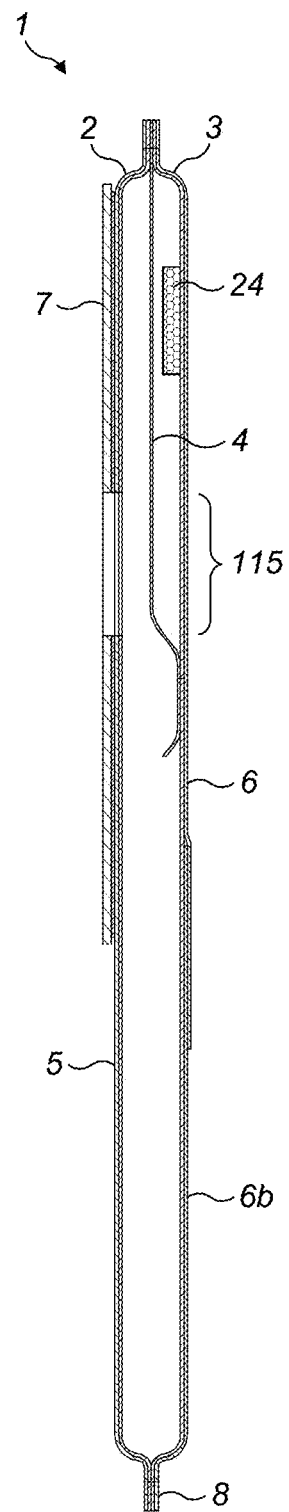
Figure 11C:
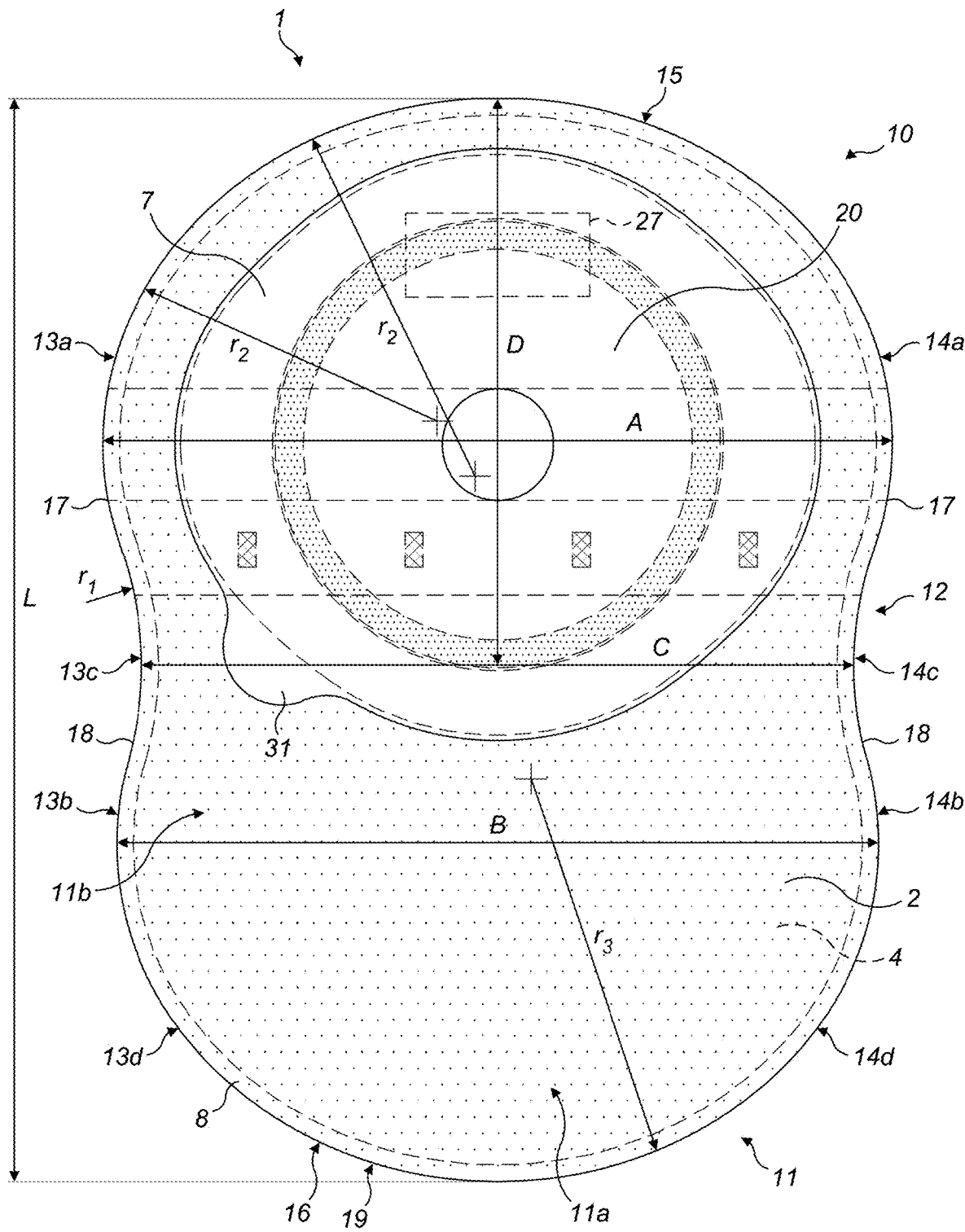

A fourth example embodiment of an ostomy appliance 1 according to the present disclosure is shown in FIGS. 11A to 11C. This example is another closed appliance.

As shown in FIGS. 11A to 11C, the ostomy appliance 1 may generally comprise an inner wall 2, an outer wall 3, a separation wall 4, an inner comfort layer 5, an outer comfort layer 6 and an ostomy wafer 7. One or more of the separation wall 4, the inner comfort layer 5 and the outer comfort layer 6 may be omitted from the ostomy appliance if desired.

The ostomy appliance 1 of this example is a one-piece appliance wherein the ostomy wafer 7 is permanently attached to the ostomy appliance 1, to the extent that the ostomy wafer 7 cannot easily be separated without risk of damaging the ostomy appliance 1. However, the teachings of this disclosure may also be applied, with suitable alteration where necessary, to a two-piece appliance. For example, where the ostomy appliance 1 is a two-piece appliance the inner wall 2, the outer wall 3, the separation wall 4, the inner comfort layer 5 and the outer comfort layer 6 may together form a pouch appliance that in use may be coupled to a body fitment component that comprises the ostomy wafer 7.

The inner wall 2 and the outer wall 3 define a cavity for containing a stomal output. The inner wall 2 and the outer wall 3 may be joined together to define the cavity. The inner wall 2 and the outer wall 3 may be formed of flexible sheet material. The flexible sheet material of the inner wall 2 and the outer wall 3 may be formed of polyurethane, polyethylene (PE), polyvinylidene chloride (PVDC) and/or ethylene-vinyl acetate (EVA). The flexible sheet material may have a thickness of 50 to 150 micrometres, preferably 75 to 100 micrometres.

As seen in FIG. 11A, the ostomy appliance 1 (and the cavity thereof) has an upper section 10, a lower section 11 and a waisted section 12 that is located between the upper section 10 and the lower section 11.

The upper section 10 has a maximum width, A. The lower section 11 has a maximum width, B. The waisted section 12 has a minimum width, C. The minimum width C is located at a distance, D from a top edge of the ostomy appliance as indicated on FIG. 11A.

According to the present disclosure, the maximum width A of the upper section 10 is greater than the maximum width B of the lower section 11 and the minimum width C of the waisted section 12 is less than the maximum width B of the lower section 11.

The waisted section 12 has a left-hand edge 13c that is smoothly rounded and a right-hand edge 14c that is smoothly rounded. Both the left-hand edge 13c and the right-hand edge 14c smoothly blend, respectively, into left-hand edges 13a, 13b and right-hand edges 14a, 14b of the upper section 10 and the lower section 11 such that the waisted section 12 smoothly merges with both the upper section 10 and the lower section 11 without abrupt changes in contour, for example as shown in FIG. 11A.

The ostomy appliance 1 of this embodiment has a length, L, of 180 mm to 240 mm, optionally of 190 mm to 230 mm, namely 194 mm. The length L is measured from the top edge to the bottom edge of the ostomy appliance 1, but could be measured from the top edge of the cavity to the bottom edge of the cavity.

The maximum width, A of the upper section 10 is from 135 mm to 150 mm, optionally 140 mm to 145 mm, namely 142 mm.

The maximum width, B of the lower section 11 is from 130 mm to 145 mm, optionally 135 mm to 140 mm, namely 137 mm.

The minimum width, C of the waisted section 12 is from 105 mm to 145 mm, optionally 110 mm to 140 mm, optionally 115 mm to 135 mm, optionally 120 mm to 130 mm, optionally 125 mm to 130 mm, namely 128 mm. This width, at the upper end of range compared to the example above has been found particularly suitable for handling relatively solid output, which could become stuck in the upper section 10 if the minimum width is too narrow. When handling output that is not especially solid, a narrower minimum width can offer better results in terms of discretion, so those skilled in the art can balance these factors as necessary, in light of this disclosure.

In this embodiment additionally to the absolute magnitudes of the dimensions A, B and C, the minimum width C of the waisted section is 5 mm to 20 mm less than the maximum width B of the lower section, optionally 5 mm to 15 mm less than the maximum width B of the lower section, optionally 8 mm to 12 mm less than the maximum width B of the lower section, namely 9 mm less than the maximum width B.

Additionally, in this embodiment the minimum width C of the waisted section 12 is 8 mm to 25 mm less than the maximum width A of the upper section, optionally 10 mm to 20 mm less than the maximum width A of the upper section, optionally 12 mm to 18 mm less than the maximum width A of the upper section, namely 14 mm less than the maximum width A of the upper section.

Additionally in this embodiment, the minimum width C of the waisted section 12 is 75% to 97% of the maximum width B of the lower section, optionally 85% to 95% of the maximum width B of the lower section, optionally 90% to 94% of the maximum width B of the lower section, namely 93% of the maximum width B of the lower section.

Additionally in this embodiment the minimum width C of the waisted section 12 is 75% to 95% of the maximum width A of the upper section, optionally 80% to 92% of the maximum width A of the upper section, optionally 85% to 90% of the maximum width A of the upper section, namely 90% of the maximum width A of the upper section.

In this embodiment, distance D, of the minimum width, C of the waisted section 12 from the top edge of the ostomy appliance is 90 mm to 130 mm, optionally 95 to 125 mm, optionally 100 to 120 mm, namely 102 mm.

Additionally in this embodiment, the distance, D of the minimum width, C of the waisted section 12 is 45% to 60% of the length, L, optionally 47% to 57% of the length, L, optionally 50% to 55% of the length, L, namely 52%.

The left-hand edge 13c and the right-hand edge 14c of the waisted section 12 may each be concavely-curved. The left-hand edge 13c and the right-hand edge 14c of the waisted section 12 may be mirror images of each other. In this embodiment the left-hand edge 13c and the right-hand edge 14c of the waisted section 12 each have a radius of curvature, $r_1$, or a blend of radii of curvature, wherein the or each radii of curvature is between 30 to 80 mm, optionally between 35 mm to 75 mm, optionally between 40 mm to 70 mm, namely 60 mm. In a similar way to the larger minimum width C in this example, this radius $r_1$ which is larger than that of the embodiments discussed above, has been found particularly suitable for handling relatively solid output, and those skilled in the art can balance the ability to handle more solid output against the overall discretion as necessary, in light of this disclosure.

The upper section 10 may be generally rounded. The upper section 10 may comprise a continuously curved edge 15 that extends from the left-hand edge 13c of the waisted section 12 to the right-hand edge 14c of the waisted section 12. The continuously curved edge 15 of the upper section 10 may be convexly curved. The continuously curved edge 15 of the upper section 10 may be absent any points of inflection or abrupt changes in contour. The continuously curved edge 15 of the upper section 10 may incorporate part or all of the left-hand edge 13a and the right-hand edge 14a of the upper section 10. In some embodiments the continuously curved edge 15 of the upper section 10 may have a radius of curvature, $r_2$, or a blend of radii of curvature, wherein the or each radii of curvature is 55 mm to 75 mm, optionally 60 to 73 mm, namely 62 mm.

As can be seen in FIG. 11A, a junction between the upper section 10 and the waisted section 12 may be demarcated by a single point of inflection 17 between the left-hand edge 13a of the upper section 10 and the left-hand edge 13c of the waisted section 12, and by a single point of inflection 17 between the right-hand edge 14a of the upper section 10 and the right-hand edge 14c of the waisted section 12. Similarly, a junction between the lower section 11 and the waisted section 12 may be demarcated by a single point of inflection 18 between the left-hand edge 13b of the lower section 11 and the left-hand edge 13c of the waisted section 12, and by a single point of inflection 18 between the right-hand edge 14b of the lower section 11 and the right-hand edge 14c of the waisted section 12.

The lower section 11 may be generally rounded. The lower section 11 may comprise a continuously curved edge 16 that extends from the left-hand edge 13c of the waisted section 12 to the right-hand edge 14c of the waisted section 12. The continuously curved edge 16 of the lower section 11 may be convexly curved. The continuously curved edge 16 of the lower section 11 may be absent any points of inflection or abrupt changes in contour. The continuously curved edge 16 of the lower section 11 may incorporate part or all of the left-hand edge 13b and the right-hand edge 14b of the lower section 11. In this embodiment the continuously curved edge 16 of the lower section 11 has a radius of curvature, $r_3$, or a blend of radii of curvature, wherein the or each radii of curvature is 45 mm to 70 mm, optionally 50 to 67 mm, namely 60.5 mm.

The inner wall 2 and the outer wall 3 may be symmetrical about a vertical midline of the ostomy appliance 1.

The inner wall 2 may be provided with a stomal inlet 20 for receiving the stomal output into the cavity. The stomal inlet 20 may be an aperture that is cut out of the inner wall 2. The stomal inlet 20 may be located within the upper section 10 of the ostomy appliance 1.

The inner wall 2 and outer wall 3 may be joined together around their peripheral edges by use of welding, adhesive or equivalent means. The inner wall 2 and the outer wall 3 may be joined together by a single continuous edge seal 8. Welding is a preferred method of joining the inner wall 2 and the outer wall 3. The single continuous edge seal 8 may extend around a full perimeter of the inner wall 2 and the outer wall 3 to create a fluid-tight seal there between. Thus, the single continuous edge seal 8 may form a closed peripheral seal which may be a closed loop. The single continuous edge seal 8 may have a width of 3 mm to 5 mm, optionally of 4 mm. The single continuous edge seal 8 may be a weld. The weld may have a constant width around the perimeter of the ostomy appliance 1.

As shown in FIG. 11C, the inner comfort layer 5 may overlie the inner wall 2 and the outer comfort layer 6 may overlie the outer wall 3.

The inner comfort layer 5 and the outer comfort layer 6 may be formed of a flexible sheet material. The flexible sheet material may comprise a fabric layer. The fabric layer may be a textile layer. The textile layer may be a woven or a non-woven textile layer. Examples of suitable materials include one or more of polyester, nylon, viscose, polyethylene and polypropylene.

The inner comfort layer 5 and the outer comfort layer 6 may comprise at least one fabric layer and at least one film layer. The at least one fabric layer may comprise a non-woven textile layer but is preferably a woven textile layer. The woven textile layer may comprise one or more of polyester, nylon, viscose, polyethylene and polypropylene. The film layer may comprise one or more of polyurethane, polyethylene (PE), polyvinylidene chloride (PVDC) and ethylene-vinyl acetate (EVA). The at least one film layer may be laminated to the at least one fabric layer, and optionally may be laminated to the at least one fabric layer over an entire area of the inner comfort layer 5 and the outer comfort layer 6.

The inner comfort layer 5 may overlie the inner wall 2. The inner comfort layer 5 may cover only a portion of the inner wall 2. However, it is preferred that the inner comfort layer 5 covers all of the inner wall 2 (except for the stomal inlet 20 of the inner wall 2).

The inner wall 2 and the inner comfort layer 5 may be joined together around their peripheral edges by use of welding, adhesive or equivalent means.

A peripheral weld may extend around the perimeter of the inner wall 2 and the inner comfort layer 5. The peripheral weld that joins the inner wall 2 with the inner comfort layer 5 may be the whole or a portion of the peripheral weld that joins the inner wall 2 and the outer wall 3.

The inner comfort layer 5 is preferably provided with a wafer aperture that is in register with the stomal inlet 20 of the inner wall 2.

The outer comfort layer 6 may overlie at least a portion of the outer wall 3. The outer wall 3 and the outer comfort layer 6 may be joined together around their peripheral edges by use of welding, adhesive or equivalent means. A peripheral weld may extend around the perimeter of the outer wall 3 and the outer comfort layer 6. The peripheral weld that joins the outer wall 3 with the outer comfort layer 6 may be the whole or a portion of the peripheral weld 8 that joins the inner wall 2 and the outer wall 3.

In some embodiments, the peripheral weld 8 may be one weld that joins together the inner comfort layer 5, the inner wall 2, the outer wall 3 and the outer comfort layer 6 (and the separation wall 4 if present).

The outer comfort layer 6 may comprise multiple parts. The external shape and dimensions of the multiple parts when taken together may be the same as that of the outer wall 3. For example, the outer comfort layer 6 may comprise an upper part 6a and a lower part 6b which may be joined to the outer wall 3 so that the upper part 6a partially overlaps the lower part 6b in an overlap region 115 as shown in FIG. 3. The upper part 6a and the lower part 6b may be separable from each other in the overlap region 115 to form a window opening for viewing the cavity. The overlap region 115 may extend horizontally when the ostomy appliance 1 is in use.

The ostomy wafer 7 may be located in register with the stomal inlet 20 of the inner wall 2. The ostomy wafer 7 may extend through the wafer aperture of the inner comfort layer 5. The ostomy wafer 7 may comprise an adhesive and a release liner 31. The ostomy wafer 7 may be mounted to the inner wall 2 by a suitable means, for example, by use of adhesive. The ostomy wafer 7 may have a generally circular shape. Alternatively the ostomy wafer 7 may have a general oval or diamond shape, wherein a width, side-to-side, of the ostomy wafer is greater than the height, top-to-bottom.

The ostomy appliance 1 may be provided with a gas vent for venting of stomal gases from the cavity. The ostomy appliance 1 may comprise a gas vent filter 24, which may be an odour filter, for example a charcoal or activated carbon filter, for reducing the release of unwanted odours from the cavity. As shown in FIG. 11C, the gas vent filter 24 may form a part of the gas vent, which may comprise at least one gas vent aperture 27 located in the outer wall 3. The gas vent filter 24 may be covered by a filter cap and the gas vent filter 24 and/or filter cap may be located on the outer wall 3 over the at least one gas vent aperture 27. The at least one gas vent aperture 27 may permit the passage of gas from the cavity towards an exterior of the ostomy appliance through the gas vent filter 24 and filter cap (if present).

The gas vent may be located, in use, in the upper half or more preferably upper quarter of the ostomy appliance 1. In particular, the centre of the at least one gas vent aperture 27 may be located, in use, above the centre of the stomal inlet 20. The term "above" is intended to mean that the at least one gas vent aperture 27 is located in use uppermost of the stomal inlet 20 along a line parallel to the inner and outer walls 2, 3 when in a flat configuration.

As shown in FIG. 11C, the separation wall 4 may be located between the inner wall 2 and the outer wall 3.

Figure 12:
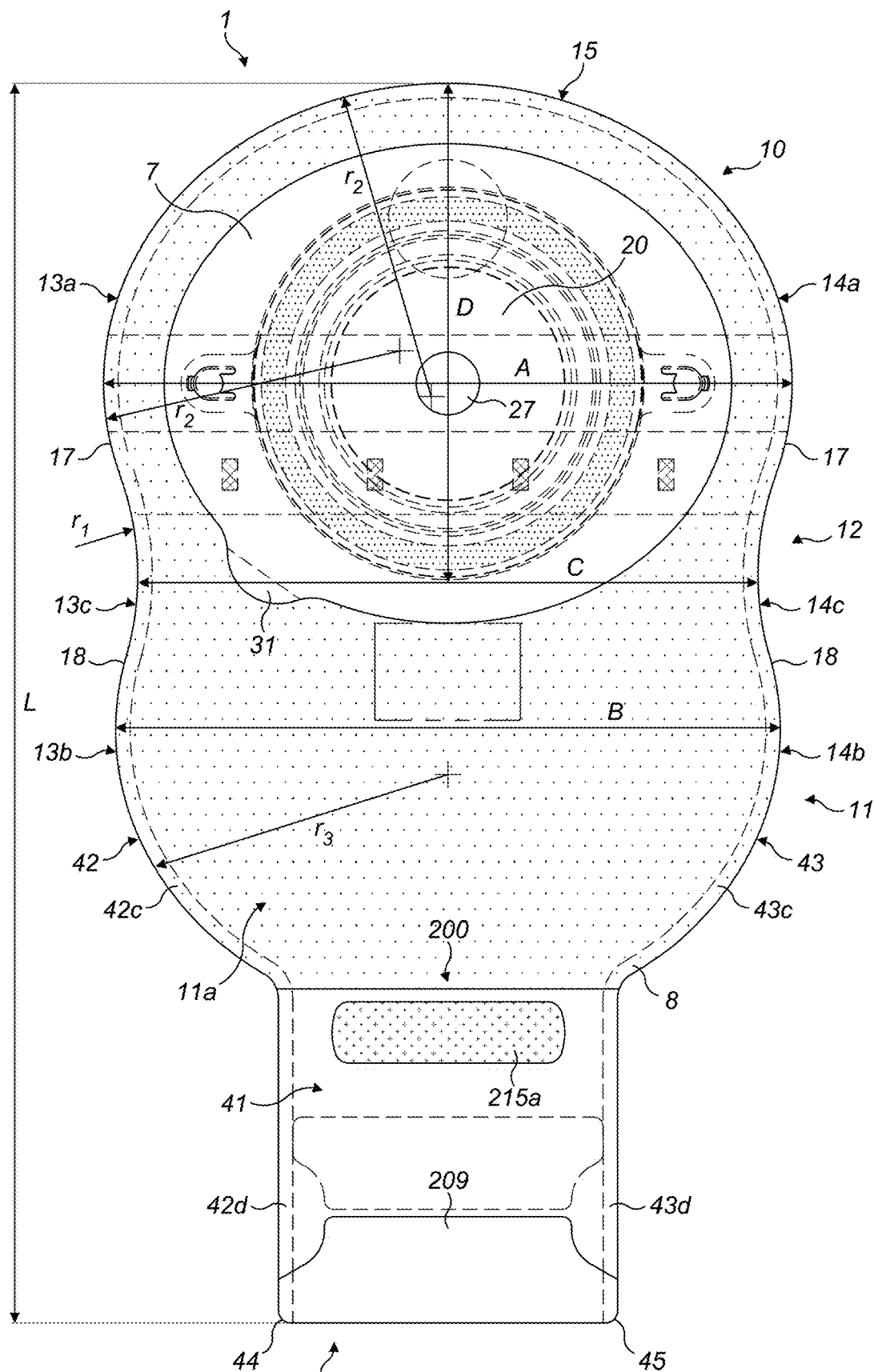
FIG. 12 is a rear view of another embodiment of an ostomy appliance according to the present disclosure.

A fifth example embodiment of an ostomy appliance 1 according to the present disclosure is shown in FIG. 12. This example is another open appliance. Like reference numerals have been used for like features. Only those features that differ in this embodiment compared to the previous embodiment will be described in detail in the following description. For features that are common to one or more embodiments, reference should be made to the description as a whole.

Essentially, the fifth embodiment has the same construction and dimensions as the fourth embodiment, but with a drain portion 41 as described in relation to the third embodiment defining an elongate drain passage that extends from the cavity of the ostomy appliance 1 to the drain aperture 40 located at a lower end of the drain portion 41.

Figure 13:
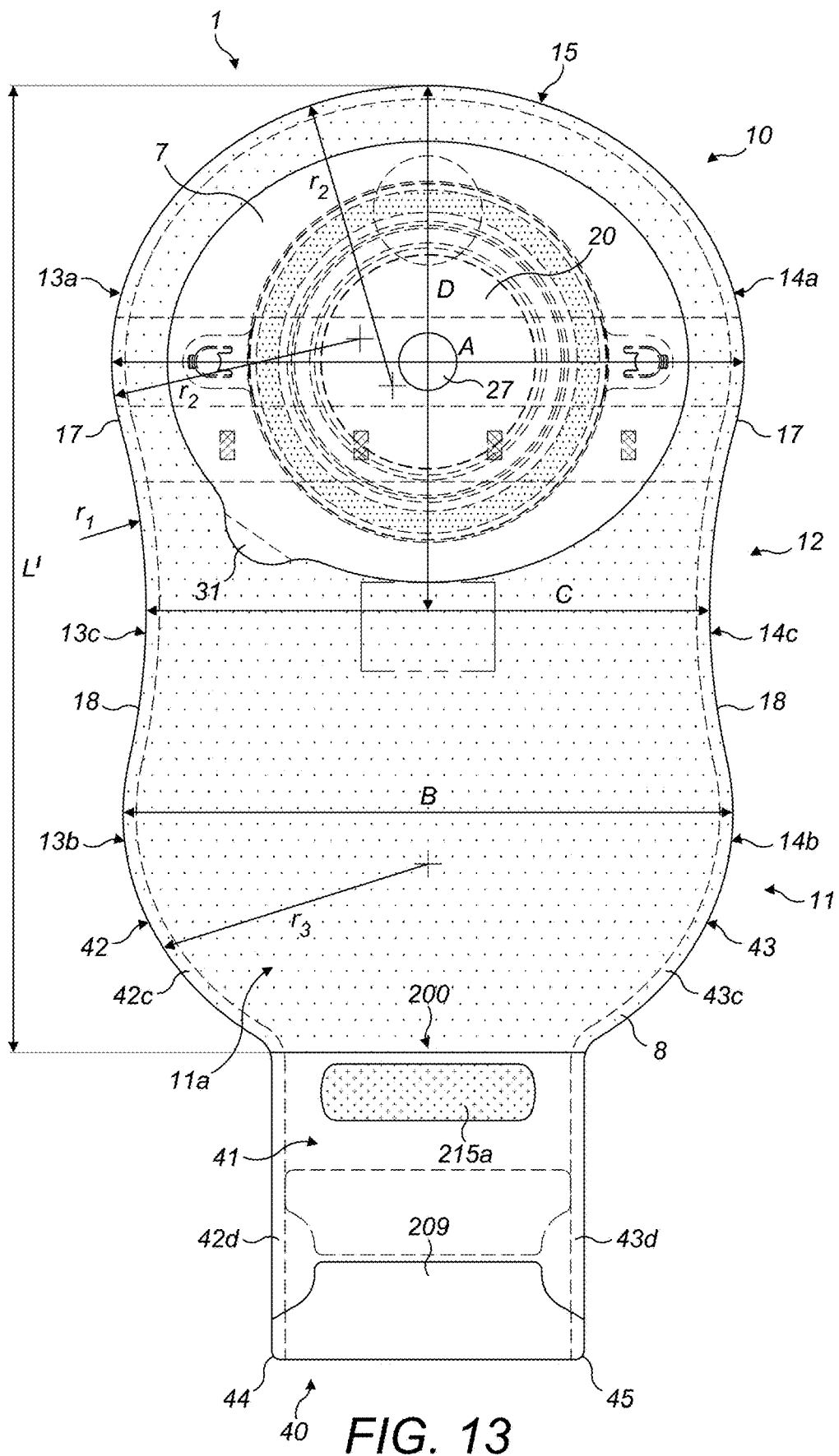
FIG. 13 is a rear view of another embodiment of an ostomy appliance according to the present disclosure.

A sixth example embodiment of an ostomy appliance 1 according to the present disclosure is shown in FIG. 13. Like reference numerals have been used for like features. Only those features that differ in this embodiment compared to the previous embodiment will be described in detail in the following description. For features that are common to one or more embodiments, reference should be made to the description as a whole.

As in all the above embodiments the maximum width, A of the upper section 10 is greater than the maximum width, B of the lower section 11 and the minimum width, C of the waisted section 12 is less than the maximum width, B, of the lower section 11.

Also, as above, the waisted section 12 has a left-hand edge 13c that is smoothly rounded and a right-hand edge 14c that is smoothly rounded. Both the left-hand edge 13c and the right-hand edge 14c smoothly blend, respectively, into left-hand edges 13a, 13b and right-hand edges 14a, 14b of the upper section 10 and the lower section 11 such that the waisted section 12 smoothly merges with both the upper section 10 and the lower section 11 without abrupt changes in contour, for example as shown in FIG. 13.

However, compared to fifth example embodiment, the waisted section 12 is shaped differently, in particular is more elongated. As can be seen in FIG. 13, this is achieved by the waisted section having a much larger radius which blends into the upper and lower sections. Specifically, the or each radii of curvature is between 30 to 200 mm, optionally between 100 mm to 175 mm, optionally between 130 mm to 160 mm, namely, 150 mm.

The maximum width dimensions A and B of the upper section 10 and lower 11 section are as defined in relation to the fourth and fifth embodiments, however, the minimum width of the waisted section is slightly smaller; from 105 mm to 145 mm, optionally 110 mm to 140 mm, optionally 115 mm to 135 mm, optionally 120 mm to 130 mm, optionally 125 mm to 130 mm, namely 126.5 mm.

In this embodiment, the minimum width C of the waisted section 12 is 5 mm to 20 mm less than the maximum width B of the lower section 11, optionally 5 mm to 15 mm less than the maximum width B of the lower section, optionally 8 mm to 12 mm less than the maximum width B of the lower section, namely 10.5 mm less than the maximum width B of the lower section.

Additionally in this embodiment the minimum width C of the waisted section 12 is 8 mm to 25 mm less than the maximum width A of the upper section 10, optionally 10 mm to 20 mm less than the maximum width A of the upper section, optionally 12 mm to 18 mm less than the maximum width A of the upper section, namely 15.5 mm less than the maximum width A of the upper section.

Additionally, in this embodiment the minimum width C of the waisted section may be 75% to 97% of the maximum width B of the lower section, optionally 85% to 95% of the maximum width B of the lower section, optionally 90% to 94% of the maximum width B of the lower section, namely 92% of the maximum width B of the lower section.

Additionally in this embodiment the minimum width C of the waisted section 12 is 75% to 95% of the maximum width A of the upper section 10, optionally 80% to 92% of the maximum width A of the upper section, optionally 85% to 90% of the maximum width A of the upper section, namely 89% of the maximum width A of the upper section.

Additionally in this embodiment a distance D of the minimum width C of the waisted section from the top edge of the ostomy appliance is 90 mm to 130 mm, optionally 95 to 125 mm, optionally 100 to 120 mm, namely 118 mm.

In this embodiment, as a consequence of the elongated waist section, the ostomy appliance 1 of this embodiment has a length of 230 mm to 300 mm when a drain of the ostomy appliance is in an unfolded configuration, optionally of 240 mm to 290 mm, namely 286 mm. In this particular embodiment the drain has a length of 69 mm, so the cavity of the open appliance is approximately equal to the length when the drain is folded, which is to say, a length of 180 mm to 240 mm, optionally of 190 mm to 230 mm, namely 217 mm.

Additionally in this embodiment the distance D of the minimum width C of the waisted section from the top edge of the ostomy appliance 1 is 45% to 60% of a length L' of the ostomy appliance in the closed configuration (i.e. the length of the cavity), optionally 47% to 57% of the length L', optionally 50% to 55% of the length L', namely 54% of the length L'.

In other respects the sixth example embodiment is the same as the fifth example embodiment described above.

Advantageously, the ostomy appliances 1 of the embodiments of present disclosure have been found to be beneficial in providing an improved level of discretion to the ostomate due to a reduced tendency for the ostomy appliance 1 to sag when filled and/or to distort or pucker in a manner that would tend to draw attention to the ostomy appliance 1 when positioned beneath clothing.

EXAMPLES

The following tables present example configurations of an ostomy appliance 1 according to the present disclosure. These examples are not intended to be limiting on the present disclosure in any way or to limit the scope of the appended claims. Rather, the examples are provided to aid a better understanding of the present disclosure.

The examples refer to features described in further detail elsewhere in the present disclosure. The skilled reader will understand that reference should be made to said further description where necessary for a fuller understanding of the examples. Where said further description refers to optional characteristics of said features then the skilled reader will understand that the following examples may optionally also include one or more of said optional characteristics.

The examples in the following table relate to ostomy appliances of the closed type and being of the general configuration of the embodiment described above with reference to FIGS. 1 to 3 and 11A to 11C:

| Example | Length, L (mm) | Dimension A (mm) | Dimension C (mm) | Dimension B (mm) | Dimension D (mm) |
|---|---|---|---|---|---|
| 1 | 208 | 142 | 129 | 137 | 99 |
| 2 | 208 | 142 | 119 | 137 | 99 |
| 3 | 208 | 142 | 109 | 137 | 99 |
| 4 | 208 | 142 | 129 | 137 | 109 |
| 5 | 208 | 142 | 119 | 137 | 109 |
| 6 | 208 | 142 | 109 | 137 | 109 |
| 7 | 208 | 142 | 129 | 137 | 119 |
| 8 | 208 | 142 | 119 | 137 | 119 |
| 9 | 208 | 142 | 109 | 137 | 119 |
| 10 | 194 | 142 | 128 | 137 | 102 |

Figure 14:
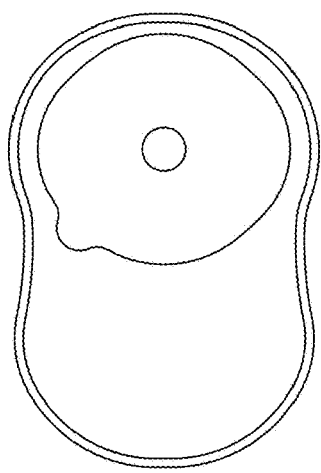
FIG. 14 shows rear view of nine examples of ostomy appliance according to the present disclosure.
Figure 14:
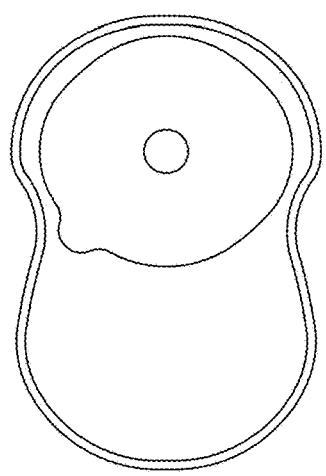
Figure 14:
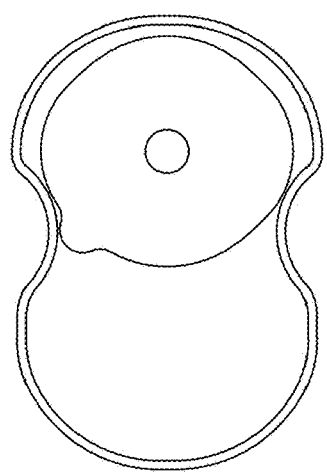
Figure 14:
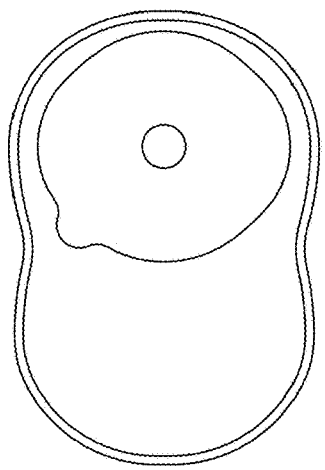
Figure 14:
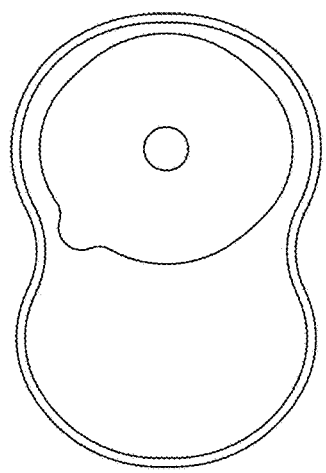
Figure 14:
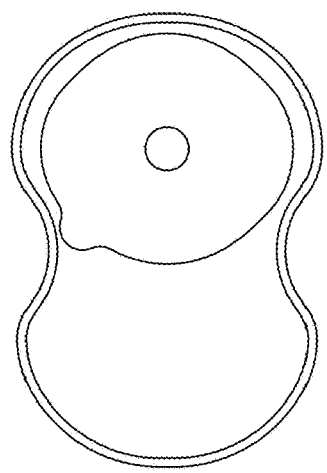
Figure 14:
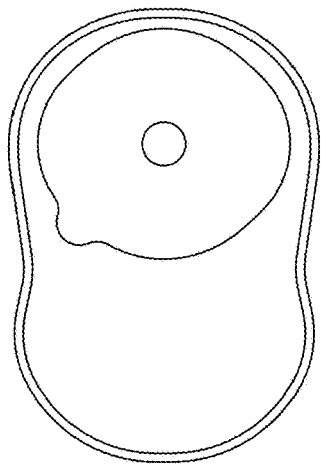
Figure 14:
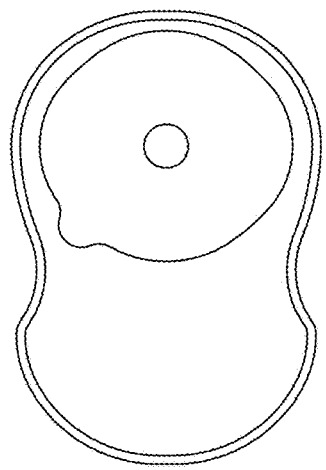
Figure 14:
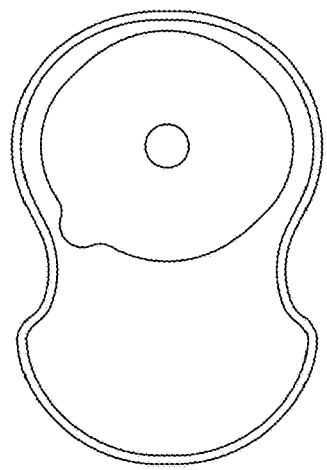
Figure 15:
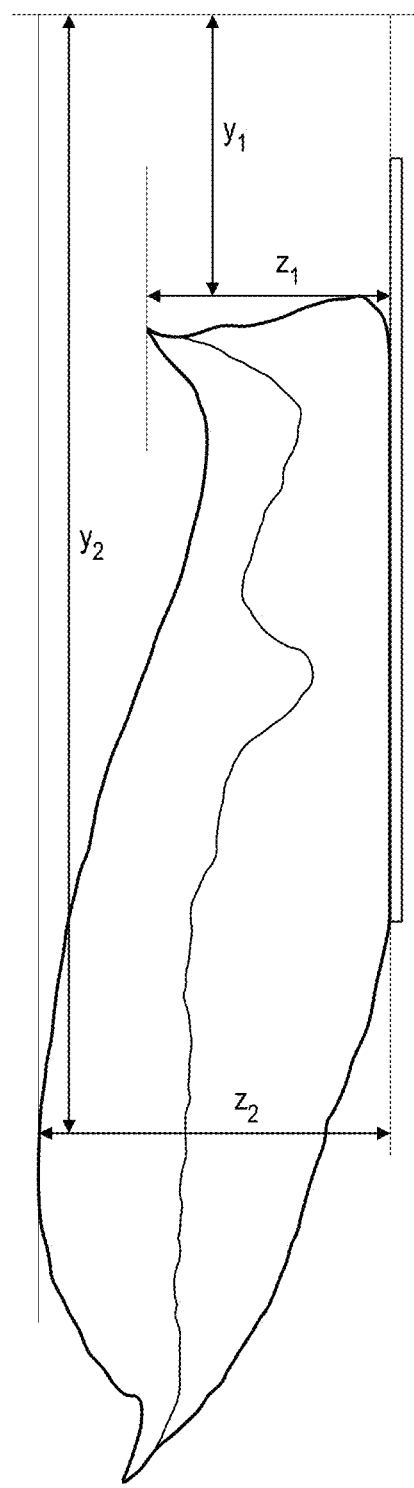
FIG. 15 is an illustration of dimensions measured when assessing the discretion profiles of the example ostomy appliances of FIG. 14.

The general configuration and shapes of Examples 1 to 10 are shown in FIG. 11A (for example 10) and FIG. 14 for Examples 1 to 9.

Examples 1 to 10 were tested to assess how discreet the ostomy appliances 1 would be in use. The examples were compared to a prior art ostomy appliance—the Salts Confidence BE® appliance available from Salts Healthcare, Birmingham, United Kingdom.

Discretion profile data for each ostomy appliance was obtained as follows:

First, the 100% fill capacity of the ostomy appliance was measured. The 100% fill capacity was measured by filling the ostomy appliance to the base of the starter hole with water. The water was then drained into a measuring cylinder and the volume measured. This volume is taken as the 100% fill capacity of the ostomy appliance.

Next, each ostomy appliance was fixed via its baseplate/wafer to a vertical test rig and then filled with water to 75% of the 100% fill capacity and measurements Y1, Y2, Z1 and Z2 as shown in FIG. 12 were taken to determine how much the ostomy appliance sagged in use:

Z1 is the distance of protrusion of the upper edge of the ostomy appliance measured perpendicular to the base plate affixed to the vertical test rig;

Z2 is the maximum distance of protrusion of the ostomy appliance measured perpendicular to the base plate affixed to the vertical test rig;

Y1 is the vertical displacement downwards of the upper edge of the ostomy appliance compared to its starting position prior to filling; and Y2 is the vertical distance of the Z2 point below the starting position of the upper edge of the ostomy appliance.

The test results are tabulated in FIG. 19.

Figure 16:
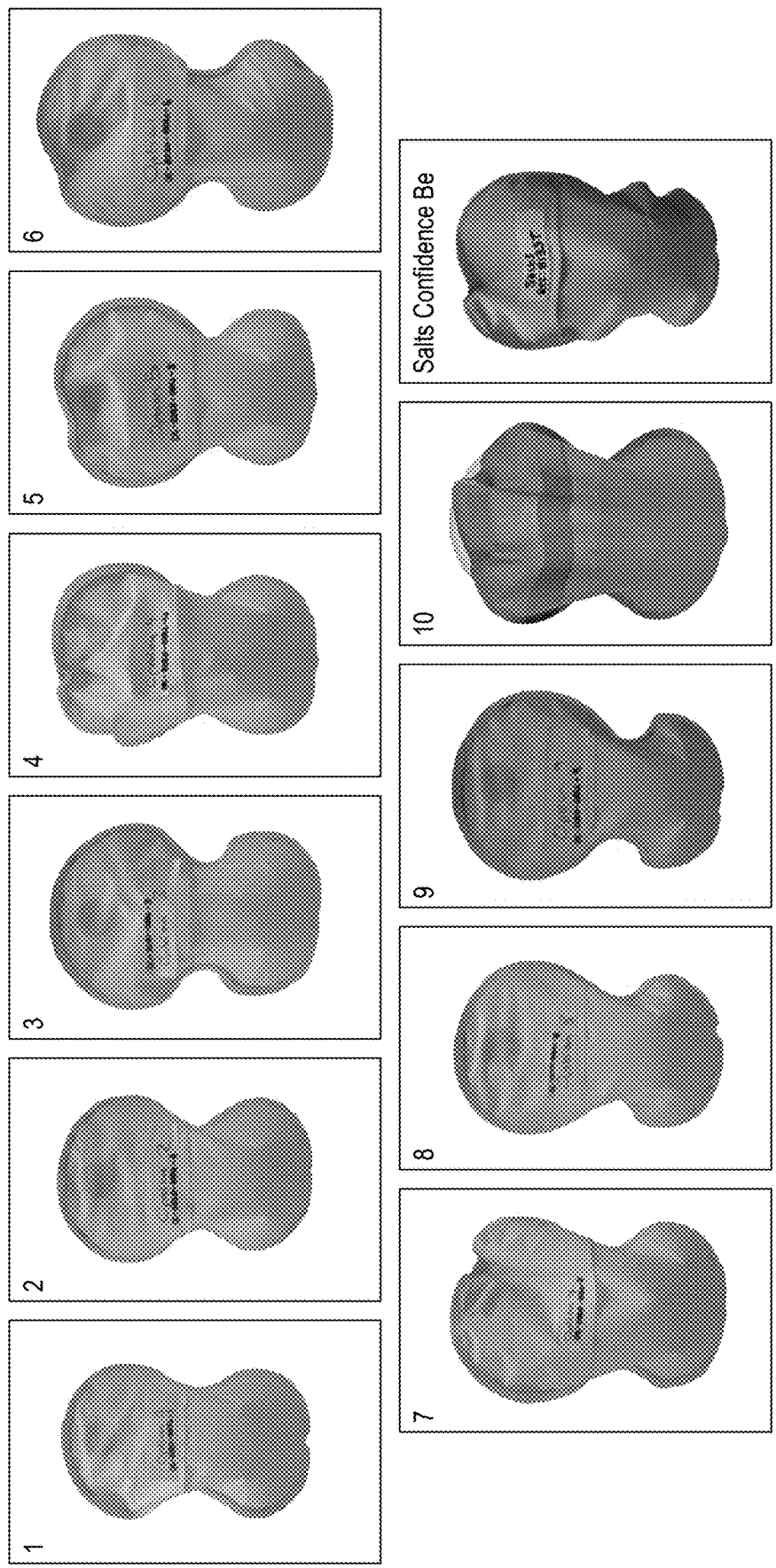
FIGS. 16 to 18 show photographs of the nine examples of ostomy appliance of FIG. 14, a tenth example according to FIGS. 11A-C and one prior art ostomy appliance during testing.
Figure 17:
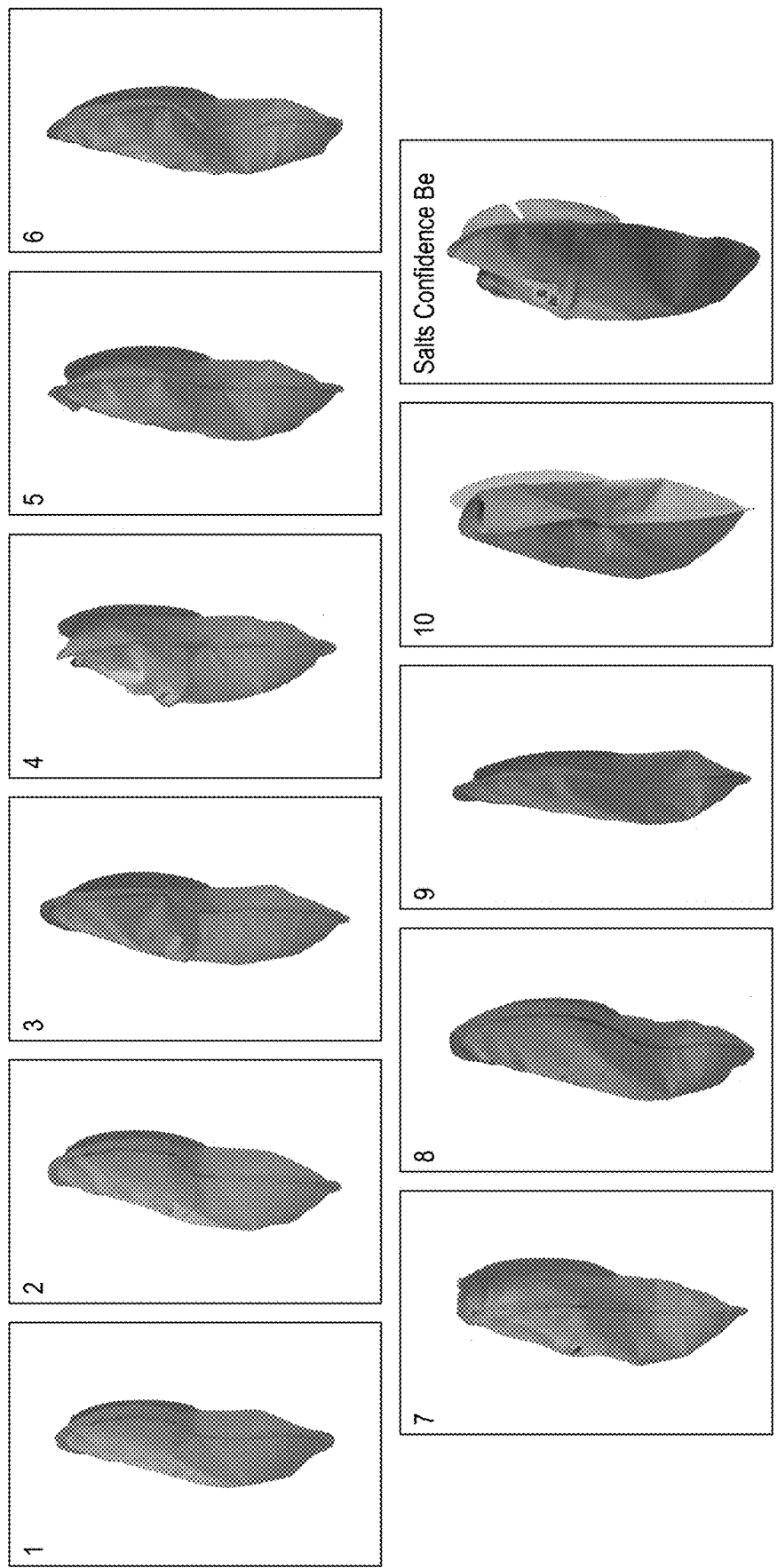
Figure 18:
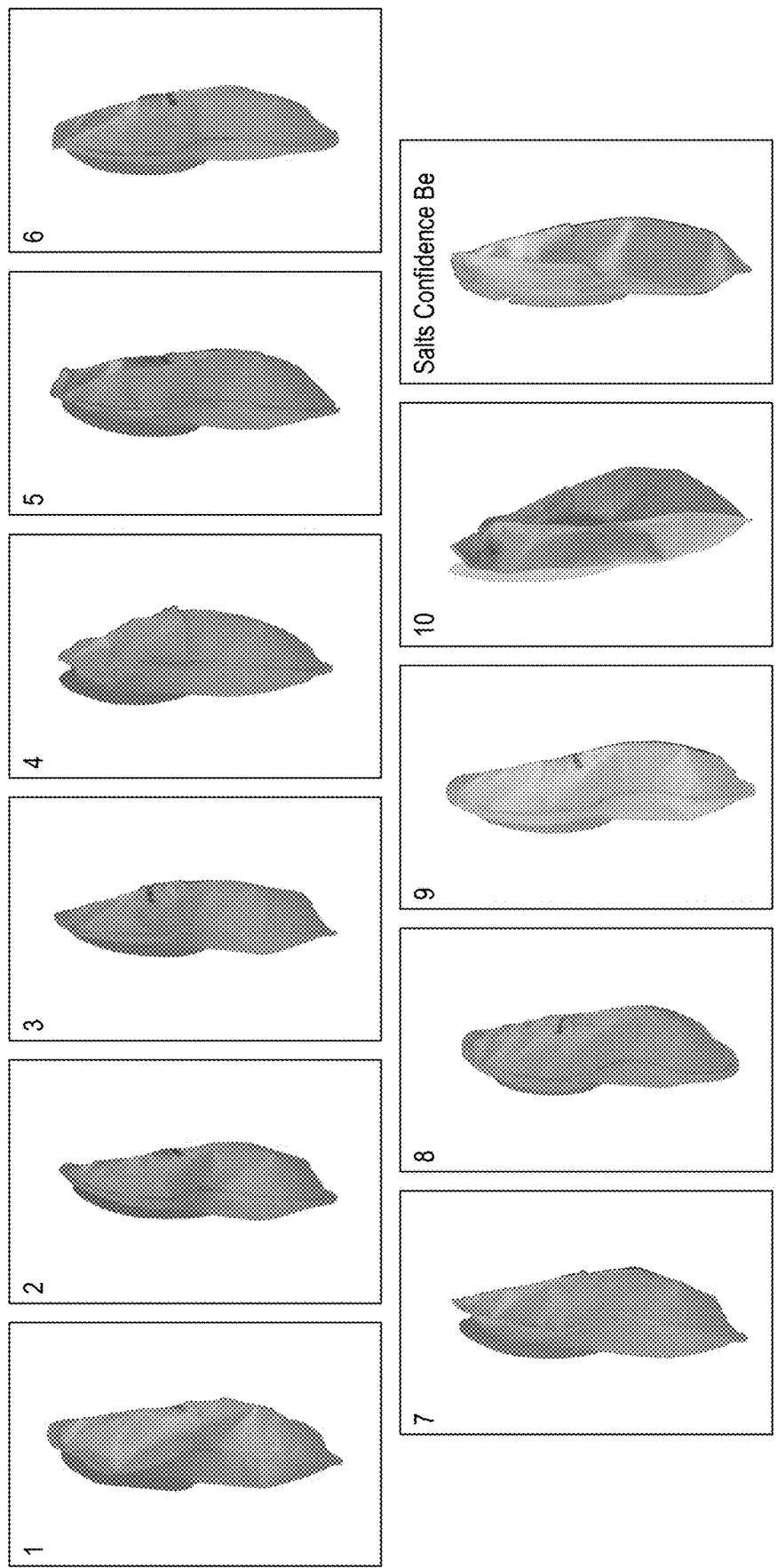

In addition, FIGS. 16 to 18 show photographs of Examples 1 to 10 and the prior art Salts Confidence BE® appliance when filled to the 75% of the 100% fill capacity. FIG. 16 shows a front view of each ostomy appliance, FIG. 17 shows a first side view of each ostomy appliance and FIG. 18 shows a second side view of each ostomy appliance. In FIGS. 16 to 18, Examples 1 to 10 are numbered '1' to '10' and the prior art Salts Confidence BE® appliance is labelled 'Salts Confidence Be'.

In terms of the discretion of use of the ostomy appliances it is considered that the Z2 measurement is the most important as ostomates typically have a high attentiveness to the maximum extent of protrusion of their ostomy appliance beneath their clothing.

To account for the different maximum capacities of the tested ostomy appliances, FIG. 19 also contains data for Z1, Z2, Y1 and Y2 normalised by the 75% fill capacity of each ostomy appliance. The 75% fill capacity is chosen rather than the 100% fill capacity since in real usage conditions ostomates will replace and/or empty their ostomy appliance before it reaches the 100% filled state.

The test results show that for the prior art Salts Confidence BES appliance Z2/75% fill capacity is 0.196 mm/ml. By contrast Examples 1 to 10 demonstrate a reduction of the Z2/75% fill capacity down to as little as 0.152 mm/ml.

As well as the maximum protrusion distance, research indicates that ostomates also pay high levels of attention to puckering and distortion of an ostomy appliance as this negatively impacts discretion by tending to produce visible creases and puckering in overlying clothing. From the test results it was observed that Examples 2 and 5, in particular, exhibit a smoother surface profile running from top to bottom of the pouch, a low degree of sagging and a more aesthetically pleasing edge profile when viewed from the front whilst also providing the desired fill volume.

The examples in the following table relate to ostomy appliances of the closed type and being of the general configuration of the embodiment described above with reference to FIGS. 4 to 6:

| Example | Length, L (mm) | Dimension A (mm) | Dimension C (mm) | Dimension B (mm) | Dimension D (mm) |
|---|---|---|---|---|---|
| 11 | 230 | 142 | 129 | 137 | 99 |
| 12 | 230 | 142 | 119 | 137 | 99 |
| 13 | 230 | 142 | 109 | 137 | 99 |
| 14 | 230 | 142 | 129 | 137 | 109 |
| 15 | 230 | 142 | 119 | 137 | 109 |
| 16 | 230 | 142 | 109 | 137 | 109 |
| 17 | 230 | 142 | 129 | 137 | 119 |
| 18 | 230 | 142 | 119 | 137 | 119 |
| 19 | 230 | 142 | 109 | 137 | 119 |

The examples in the following table relate to ostomy appliances of the open type and being of the general configuration of the embodiment described above with reference to FIGS. 7 to 10:

| Example | Length, L (mm) | Dimension A (mm) | Dimension C (mm) | Dimension B (mm) | Dimension D (mm) |
|---|---|---|---|---|---|
| 20 | 290 | 142 | 129 | 137 | 99 |
| 21 | 290 | 142 | 119 | 137 | 99 |
| 22 | 290 | 142 | 109 | 137 | 99 |
| 23 | 290 | 142 | 129 | 137 | 109 |
| 24 | 290 | 142 | 119 | 137 | 109 |
| 25 | 290 | 142 | 109 | 137 | 109 |
| 26 | 290 | 142 | 129 | 137 | 119 |
| 27 | 290 | 142 | 119 | 137 | 119 |
| 28 | 290 | 142 | 109 | 137 | 119 |

The examples in the following table relate to further ostomy appliance of the open type:

| Example | Length, L (mm) | Dimension A (mm) | Dimension C (mm) | Dimension B (mm) | Dimension D (mm) |
|---|---|---|---|---|---|
| 29 | 320 | 142 | 129 | 137 | 99 |
| 30 | 320 | 142 | 119 | 137 | 99 |
| 31 | 320 | 142 | 109 | 137 | 99 |
| 32 | 320 | 142 | 129 | 137 | 109 |
| 33 | 320 | 142 | 119 | 137 | 109 |
| 34 | 320 | 142 | 109 | 137 | 109 |
| 35 | 320 | 142 | 129 | 137 | 119 |
| 36 | 320 | 142 | 119 | 137 | 119 |
| 37 | 320 | 142 | 109 | 137 | 119 |

Further aspects of the present disclosure are set out in the following clauses.

CLAUSES

Clause 1. An ostomy appliance comprising an inner wall and an outer wall that define a cavity for containing a stomal output,
the ostomy appliance having an upper section, a lower section and a waisted section that is located between the upper section and the lower section;
the inner wall comprising, within the upper section, an inlet for receiving the stomal output into the cavity;
the upper section having a maximum width (A) that is greater than a maximum width (B) of the lower section;
the waisted section having a minimum width (C) that is less than the maximum width (B) of the lower section; and
the waisted section having a left-hand edge that is smoothly rounded and a right-hand edge that is smoothly rounded, and that both the left-hand edge and the right-hand edge smoothly blend, respectively, into left-hand edges and right-hand edges of the upper section and the lower section.

Clause 2. The ostomy appliance of clause 1, wherein the ostomy appliance is a closed appliance and has a length of 200 mm to 240 mm, optionally of 205 mm to 235 mm, optionally 208 mm or 230 mm.

Clause 3. The ostomy appliance of clause 1, wherein the ostomy appliance is a closed appliance and has a length of 180 mm to 240 mm, optionally of 190 mm to 230 mm, optionally 194 mm or 224 mm.

Clause 4. The ostomy appliance of clause 1, wherein the ostomy appliance is an open appliance with a foldable drain, and has a length of 250 mm to 300 mm when a drain of the ostomy appliance is in an unfolded configuration, optionally a length of 290 mm.

Clause 5. The ostomy appliance of clause 1, wherein the ostomy appliance is an open appliance with a foldable drain, and has a length of 230 mm to 300 mm when a drain of the ostomy appliance is in an unfolded configuration, optionally of 240 mm to 290 mm, optionally a length of 256 mm or 286 mm.

Clause 6. The ostomy appliance of any preceding clause, wherein the maximum width (A) of the upper section is 135 mm to 150 mm, optionally 140 mm to 145 mm, optionally 142 mm.

Clause 7. The ostomy appliance of any preceding clause, wherein the maximum width (B) of the lower section is 130 mm to 145 mm, optionally 135 mm to 140 mm, optionally 137 mm to 139 mm.

Clause 8. The ostomy appliance of any preceding clause, wherein the minimum width (C) of the waisted section is 105 mm to 135 mm, optionally 110 mm to 130 mm, optionally 110 mm to 125 mm, optionally 115 mm to 130 mm, optionally 120 mm to 135 mm, optionally 115 mm to 120 mm, optionally 120 mm to 125 mm, optionally 125 mm to 130 mm, optionally 120 mm, optionally 129 mm, optionally 119 mm, optionally 109 mm.

Clause 9. The ostomy appliance of any preceding clause, wherein the minimum width (C) of the waisted section is 5 mm to 30 mm less than the maximum width (B) of the lower section, optionally 10 mm to 20 mm less than the maximum width (B) of the lower section, optionally 15 mm to 20 mm less than the maximum width (B) of the lower section.

Clause 10. The ostomy appliance of any preceding clause, wherein the minimum width (C) of the waisted section is 10 mm to 35 mm less than the maximum width (A) of the upper section, optionally 15 mm to 30 mm less than the maximum width (A) of the upper section, optionally 20 mm to 25 mm less than the maximum width (A) of the upper section.

Clause 11. The ostomy appliance of any preceding clause, wherein the minimum width (C) of the waisted section is 75% to 95% of the maximum width (B) of the lower section, optionally 80% to 90% of the maximum width (B) of the lower section, optionally 83% to 88% of the maximum width (B) of the lower section.

Clause 12. The ostomy appliance of any preceding clause, wherein the minimum width (C) of the waisted section is 73% to 92% of the maximum width (A) of the upper section, optionally 75% to 85% of the maximum width (A) of the upper section, optionally 80% to 85% of the maximum width (A) of the upper section.

Clause 13. The ostomy appliance of any preceding clause, wherein a distance (D) of the minimum width (C) of the waisted section from the top edge of the ostomy appliance may be 90 mm to 125 mm, optionally 95 to 120 mm, optionally 105 to 115 mm, optionally 99 mm, optionally 109 mm, optionally 119 mm.

Clause 14. The ostomy appliance of any preceding clause, wherein a distance (D) of the minimum width (C) of the waisted section from the top edge of the ostomy appliance may be 45% to 60% of a length (L) of the ostomy appliance, optionally 47% to 57% of the length (L), optionally 50% to 55% of the length (L).

Clause 15. The ostomy appliance of any preceding clause, wherein the left-hand edge and the right-hand edge of the waisted section are each concavely-curved.

Clause 16. The ostomy appliance of any preceding clause, wherein the left-hand edge and the right-hand edge of the waisted section each have a radius of curvature, or a blend of radii of curvature, wherein the or each radii of curvature is 35 mm to 45 mm, optionally 40 mm.

Clause 17. The ostomy appliance of any preceding clause, wherein the left-hand edge and the right-hand edge of the waisted section each have a radius of curvature, or a blend of radii of curvature, wherein the or each radii of curvature is between 30 to 80 mm, optionally between 35 mm to 75 mm, optionally between 40 mm to 70 mm, optionally 60 mm.

Clause 18. The ostomy appliance of any preceding clause, wherein the left-hand edge and the right-hand edge of the waisted section are mirror images of each other.

Clause 19. The ostomy appliance of any preceding clause, wherein the upper section is generally rounded.

Clause 20. The ostomy appliance of any preceding clause, wherein the upper section comprises a continuously curved edge that extends from the left-hand edge of the waisted section to the right-hand edge of the waisted section.

Clause 21. The ostomy appliance of clause 20, wherein the continuously curved edge of the upper section is convexly curved.

Clause 22. The ostomy appliance of clause 20 or clause 21, wherein the continuously curved edge of the upper section is absent any points of inflection or abrupt changes in contour.

Clause 23. The ostomy appliance of any one of clauses 20 to 22, wherein the continuously curved edge of the upper section has a radius of curvature, or a blend of radii of curvature, wherein the or each radii of curvature is 55 mm to 75 mm, optionally 60 to 73 mm.

Clause 24. The ostomy appliance of any preceding clause, wherein a junction between the upper section and the waisted section is demarcated by a single point of inflection between the left-hand edge of the upper section and the left-hand edge of the waisted section, and by a single point of inflection between the right-hand edge of the upper section and the right-hand edge of the waisted section.

Clause 25. The ostomy appliance of any preceding clause, wherein a junction between the lower section and the waisted section is demarcated by a single point of inflection between the left-hand edge of the lower section and the left-hand edge of the waisted section, and by a single point of inflection between the right-hand edge of the lower section and the right-hand edge of the waisted section.

Clause 26. The ostomy appliance of any preceding clause, wherein the lower section is generally rounded.

Clause 27. The ostomy appliance of any preceding clause, wherein the lower section comprises a continuously curved edge that extends from the left-hand edge of the waisted section to the right-hand edge of the waisted section.

Clause 28. The ostomy appliance of any preceding clause, wherein the continuously curved edge of the lower section is convexly curved.

Clause 29. The ostomy appliance of any preceding clause, wherein the continuously curved edge of the lower section is absent any points of inflection or abrupt changes in contour.

Clause 30. The ostomy appliance of any preceding clause, wherein the continuously curved edge of the lower section has a radius of curvature, or a blend of radii of curvature, wherein the or each radii of curvature is 45 mm to 70 mm, optionally 50 to 67 mm.

Clause 31. The ostomy appliance of any one of clauses 1 to 25, wherein the lower section comprises a generally rounded portion and a generally rectangular portion, with the generally rectangular portion being adjacent the waisted section and generally rounded portion being distal the waisted section.

Clause 32. The ostomy appliance of clause 31, wherein the lower section comprises a continuous lower edge that extends from the left-hand edge of the waisted section along a left-hand edge of the generally rectangular portion, around a continuously curved edge of the generally rounded portion and along a right-hand edge of the generally rectangular portion to the right-hand edge of the waisted section.

Clause 33. The ostomy appliance of clause 32, wherein the continuously curved edge of the generally rounded portion is convexly curved.

Clause 34. The ostomy appliance of clause 32 or clause 33, wherein the continuously curved edge of the generally rounded portion is absent any points of inflection or abrupt changes in contour.

Clause 35. The ostomy appliance of any one of clauses 32 to 34, wherein the continuously curved edge of the generally rounded portion has a radius of curvature, or a blend of radii of curvature, wherein the or each radii of curvature is 55 mm to 70 mm, optionally 67 mm.

Clause 36. The ostomy appliance of any one of clauses 1 to 25, wherein the lower section comprises a drain aperture.

Clause 37. The ostomy appliance of clause 36, wherein the lower section comprises a generally rounded portion and a drain portion that accommodates the drain aperture, with the generally rounded portion being adjacent the waisted section and the drain portion being distal the waisted section.

Clause 38. The ostomy appliance of clause 37, wherein the lower section comprises a continuous left-hand edge that extends from the left-hand edge of the waisted section around a left-hand edge of the generally rounded portion and along a left-hand edge of the drain portion, and further comprises a continuous right-hand edge that extends from the right-hand edge of the waisted section around a right-hand edge of the generally rounded portion and along a right-hand edge of the drain portion.

Clause 39. The ostomy appliance of clause 38, wherein the left-hand edge and the right-hand edge of the generally rounded portion each have a radius of curvature, or a blend of radii of curvature, wherein the or each radii of curvature is 45 mm to 70 mm, optionally 50 to 67 mm.

Clause 40. The ostomy appliance of any preceding clause, wherein the inner wall and the outer wall are symmetrical about a vertical midline of the ostomy appliance.

Clause 41. The ostomy appliance of any preceding clause, wherein the inner wall and the outer wall are joined together by a single continuous edge seal.

Clause 42. The ostomy appliance of any preceding clause, wherein the ostomy appliance is a closed appliance and the single continuous edge seal forms a closed peripheral seal.

Clause 43. The ostomy appliance of any one of clauses 1 to 41, wherein the ostomy appliance is an open appliance and the single continuous edge seal extend from a left-hand edge of a drain aperture to a right-hand edge of a drain aperture.

Clause 44. The ostomy appliance of any preceding clause, wherein the single continuous edge seal is a weld, optionally a weld having a width of 3 mm to 5 mm, optionally of 4 mm.

Clause 45. The ostomy appliance of any preceding clause, wherein the inner wall and the outer wall are formed from flexible sheet material.

Clause 46. The ostomy appliance of any preceding clause, further comprising either an ostomy wafer that is located in register with the inlet of the inner wall, or a releasable coupling that is located in register with the inlet of the inner wall and that is configured for coupling with a body fitment component comprising an ostomy wafer.

Clause 47. The ostomy appliance of any preceding clause, further comprising at least one comfort layer overlying at least one of the inner wall and the outer wall.

Clause 48. The ostomy appliance of any preceding clause, wherein the cavity comprises the upper section, the lower section, and the waisted section located between the upper section and the lower section.

It is to be understood that at least some of the figures and descriptions of the disclosure have been simplified to focus on elements that are relevant for a clear understanding of the disclosure, while eliminating, for purposes of clarity, other elements that the reader skilled in the art will appreciate may also be required. Because such elements are well known to the reader skilled in the art, and because they do not necessarily facilitate a better understanding of the disclosure, a description of such elements is not provided herein.

The invention claimed is:

1. An ostomy appliance comprising:
an inner wall and an outer wall that define a cavity for containing a stomal output, the ostomy appliance having an upper section, a lower section and a waisted section that is located between the upper section and the lower section;
the inner wall comprising, within the upper section:
an inlet for receiving the stomal output into the cavity;
the upper section having a maximum width (A) that is greater than a maximum width (B) of the lower section;
the waisted section having a minimum width (C) that is less than the maximum width (B) of the lower section; and
the waisted section having a left-hand edge that is smoothly rounded and a right-hand edge that is smoothly rounded, and that both the left-hand edge and the right-hand edge smoothly blend, respectively, into left-hand edges and right-hand edges of the upper section and the lower section;
wherein the left-hand edge and the right-hand edge of the waisted section are each concavely-curved having a radius of curvature of 30 mm or greater.

2. The ostomy appliance of claim 1, wherein the cavity comprises the upper section, the lower section, and the waisted section located between the upper section and the lower section.

3. The ostomy appliance of claim 1, wherein the maximum width (A) of the upper section is 135 mm to 150 mm.

4. The ostomy appliance of claim 1, wherein the maximum width (B) of the lower section is 130 mm to 145 mm.

5. The ostomy appliance of claim 1, wherein the minimum width (C) of the waisted section is 105 mm to 135 mm.

6. The ostomy appliance of claim 1, wherein the minimum width (C) of the waisted section is 5 mm to 30 mm less than the maximum width (B) of the lower section.

7. The ostomy appliance of claim 1, wherein the upper section comprises a continuously curved edge that extends from the left-hand edge of the waisted section to the right-hand edge of the waisted section.

8. The ostomy appliance of claim 7, wherein the continuously curved edge of the upper section is convexly curved.

9. The ostomy appliance of claim 1, wherein the lower section comprises a continuously curved edge that extends from the left-hand edge of the waisted section to the right-hand edge of the waisted section.

10. The ostomy appliance of claim 1, wherein the continuously curved edge of the lower section is convexly curved.

11. The ostomy appliance of claim 1, wherein the lower section comprises a drain aperture.

12. The ostomy appliance of claim 11, wherein the lower section comprises a generally rounded portion and a drain portion that accommodates the drain aperture, with the generally rounded portion being adjacent the waisted section and the drain portion being distal the waisted section.

13. The ostomy appliance of claim 12, wherein the lower section comprises a continuous left-hand edge that extends from the left-hand edge of the waisted section around a left-hand edge of the generally rounded portion and along a left-hand edge of the drain portion, and further comprises a continuous right-hand edge that extends from the right-hand edge of the waisted section around a right-hand edge of the generally rounded portion and along a right-hand edge of the drain portion.

14. The ostomy appliance of claim 1, wherein the inner wall and the outer wall are symmetrical about a vertical midline of the ostomy appliance.

15. The ostomy appliance of claim 1, wherein the inner wall and the outer wall are joined together by a single continuous edge seal.

16. The ostomy appliance of claim 1, further comprising either an ostomy wafer that is located in register with the inlet of the inner wall, or a releasable coupling that is located in register with the inlet of the inner wall and that is configured for coupling with a body fitment component comprising an ostomy wafer.

17. The ostomy appliance of claim 1, wherein the ostomy appliance is a closed appliance and has a length of 180 mm to 240 mm.

18. The ostomy appliance of claim 1, wherein the ostomy appliance is an open appliance with a foldable drain, and has a length of 230 mm to 300 mm when a drain of the ostomy appliance is in an unfolded configuration.

19. The ostomy appliance of claim 18, wherein the open ostomy appliance has length of 180 mm to 240 mm when a drain of the ostomy appliance is in a folded configuration.

* * * * *